United States Patent
Tojo

(10) Patent No.: US 10,188,315 B2
(45) Date of Patent: Jan. 29, 2019

(54) INSERTION SYSTEM HAVING INSERTION PORTION AND INSERTION MEMBER

(71) Applicant: OLYMPUS CORPORATION, Tokyo (JP)

(72) Inventor: Ryo Tojo, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 715 days.

(21) Appl. No.: 14/682,558

(22) Filed: Apr. 9, 2015

(65) Prior Publication Data
US 2015/0208947 A1 Jul. 30, 2015

Related U.S. Application Data

(63) Continuation of application No. PCT/JP2013/076884, filed on Oct. 2, 2013.

(30) Foreign Application Priority Data

Oct. 10, 2012 (JP) .................................. 2012-225460

(51) Int. Cl.
*A61B 1/04* (2006.01)
*A61B 5/06* (2006.01)
(Continued)

(52) U.S. Cl.
CPC .......... *A61B 5/065* (2013.01); *A61B 1/00071* (2013.01); *A61B 1/00133* (2013.01);
(Continued)

(58) Field of Classification Search
USPC ................................ 600/103, 112, 117, 153
See application file for complete search history.

(56) References Cited

U.S. PATENT DOCUMENTS

2009/0018390 A1  1/2009  Honda et al.
2009/0326319 A1  12/2009 Takahashi et al.

FOREIGN PATENT DOCUMENTS

CN    101621955 A    1/2010
EP    2 116 174 A1   11/2009
(Continued)

OTHER PUBLICATIONS

Chinese Office Action dated Mar. 15, 2016 in related Chinese Patent Application No. 201380053226.1.
(Continued)

*Primary Examiner* — Timothy J Neal
*Assistant Examiner* — Jae Woo
(74) *Attorney, Agent, or Firm* — Scully, Scott, Murphy & Presser, P.C.

(57) ABSTRACT

To accurately recognize the position and direction of an insertion member, there is provided an insertion system which detects operation support information such as an insertion amount and a rotation amount of the insertion member, and the position and shape of the distal end thereof. The insertion system includes an insertion portion including at least a grasp portion, an insertion portion to be inserted into a specimen, an insertion channel passing from the proximal end of the insertion portion to the distal end, the insertion member to be inserted into the insertion channel, a first state detector which is disposed in the insertion portion and which detects information to calculate at least one of an insertion amount of the inserted insertion member in an insertion direction along a longitudinal direction and a rotation amount of the insertion member around its central axis along the insertion direction, and a calculation unit which calculates operation support information from a detection result by the first state detector.

11 Claims, 13 Drawing Sheets

(51) Int. Cl.
  *G02B 23/24* (2006.01)
  *G02B 27/32* (2006.01)
  *A61B 1/018* (2006.01)
  *A61B 1/00* (2006.01)
  *A61B 17/00* (2006.01)
  *A61B 34/00* (2016.01)
  *A61B 90/00* (2016.01)
  *A61B 34/20* (2016.01)

(52) U.S. Cl.
  CPC .......... *A61B 1/00163* (2013.01); *A61B 1/018* (2013.01); *G02B 23/2476* (2013.01); *G02B 27/32* (2013.01); *A61B 34/70* (2016.02); *A61B 2017/00199* (2013.01); *A61B 2034/2061* (2016.02); *A61B 2090/061* (2016.02); *A61B 2090/067* (2016.02)

(56) References Cited

FOREIGN PATENT DOCUMENTS

| | | |
|---|---|---|
| EP | 2 147 630 A2 | 1/2010 |
| JP | 59-7919 A | 1/1984 |
| JP | 2003-088493 A | 3/2003 |
| JP | 2004-105725 A | 4/2004 |
| JP | 2007-111551 A | 5/2007 |
| JP | 2007-159738 A | 6/2007 |
| JP | 2009-011809 A | 1/2009 |
| JP | 2009-279250 A | 12/2009 |
| JP | 2010-022619 A | 2/2010 |
| JP | 2010-022762 A | 2/2010 |
| JP | 2011-104053 A | 6/2011 |
| JP | 2012-115521 A | 6/2012 |

OTHER PUBLICATIONS

Japanese Office Action dated Aug. 23, 2016 in related Japanese Patent Application No. 2012-225460.

Chinese Office Action dated Nov. 17, 2016 in related Chinese Patent Application No. 201380053226.1.

English translation of International Preliminary Report on Patentability dated Apr. 23, 2015 together with the Written Opinion received in related International Application No. PCT/JP2013/076884.

International Search Report dated Dec. 24, 2013 issued in PCT/JP2013/076884.

Extended Supplementary European Search Report dated May 30, 2016 in related European Application No. 13 84 5047.3.

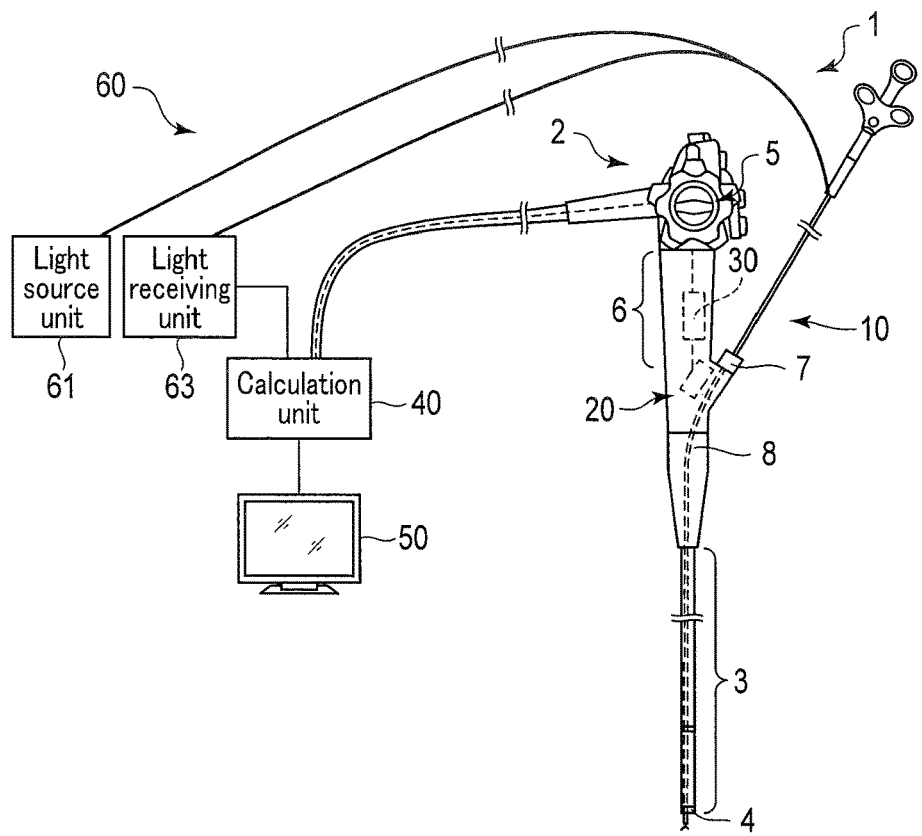
F I G. 1
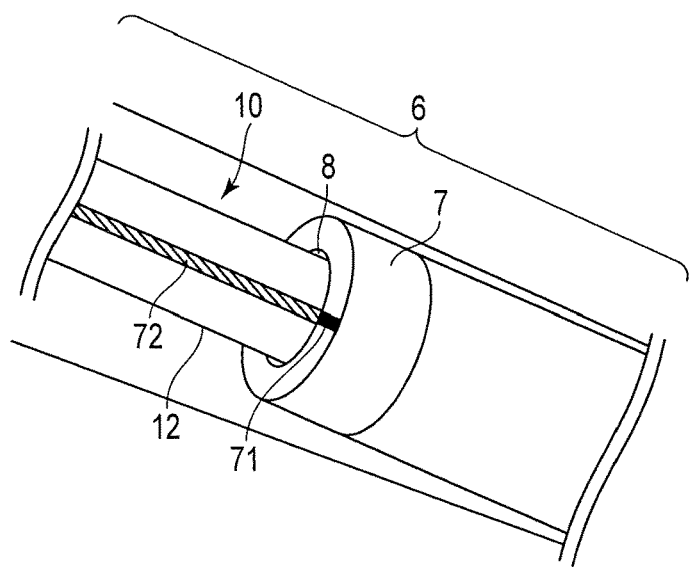
F I G. 2

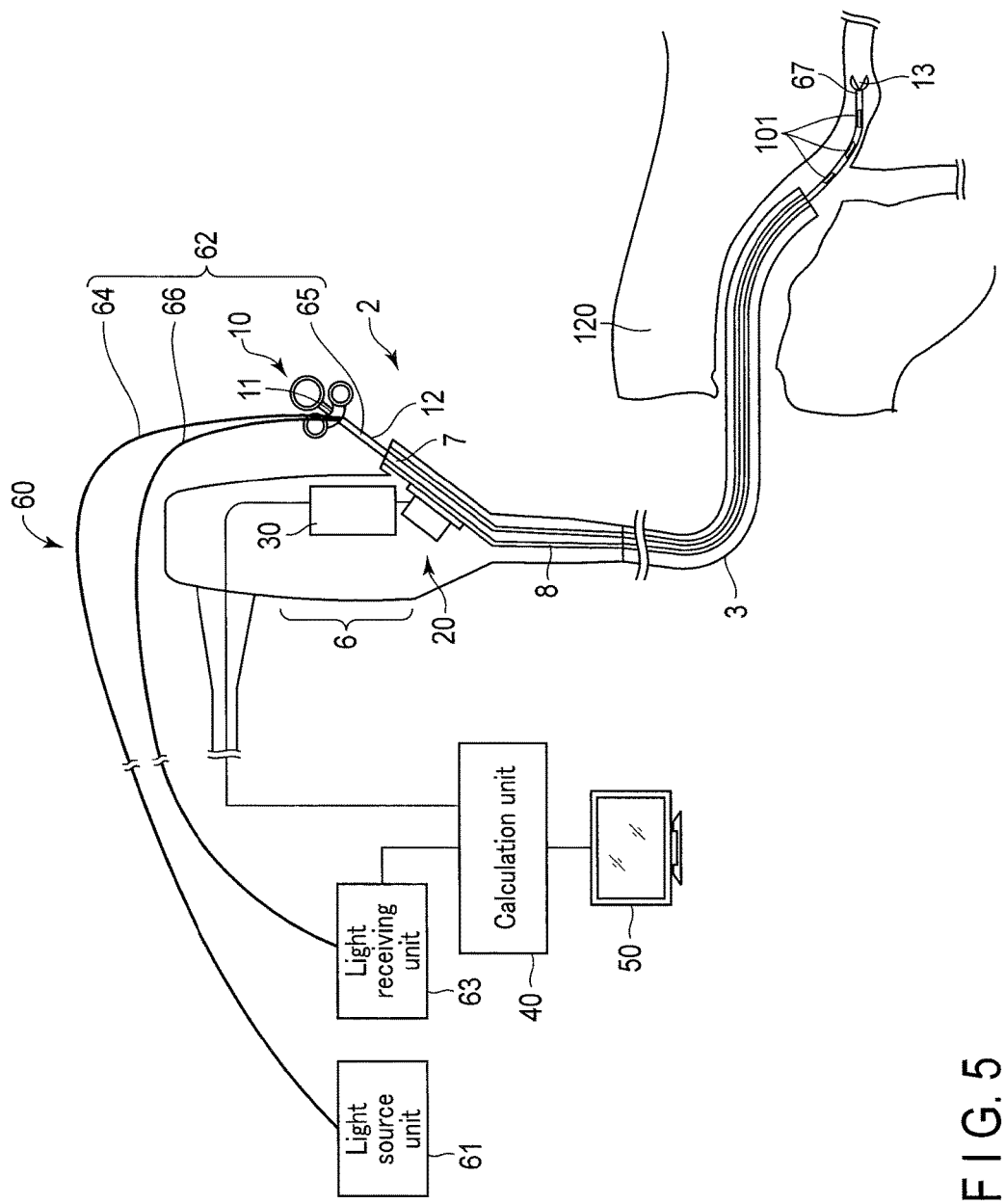
F I G. 5

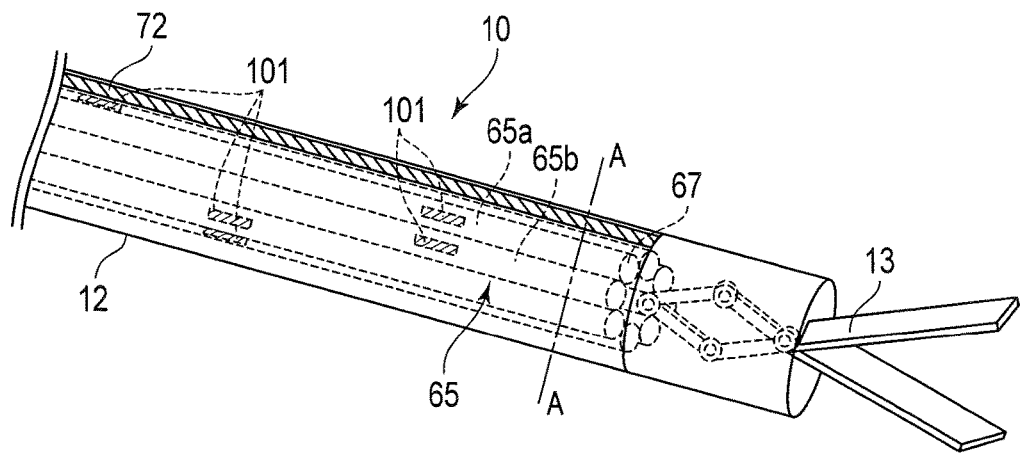
F I G. 6A
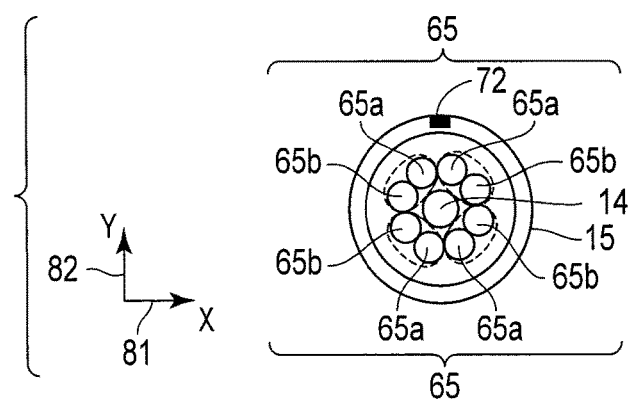
A-A
F I G. 6B

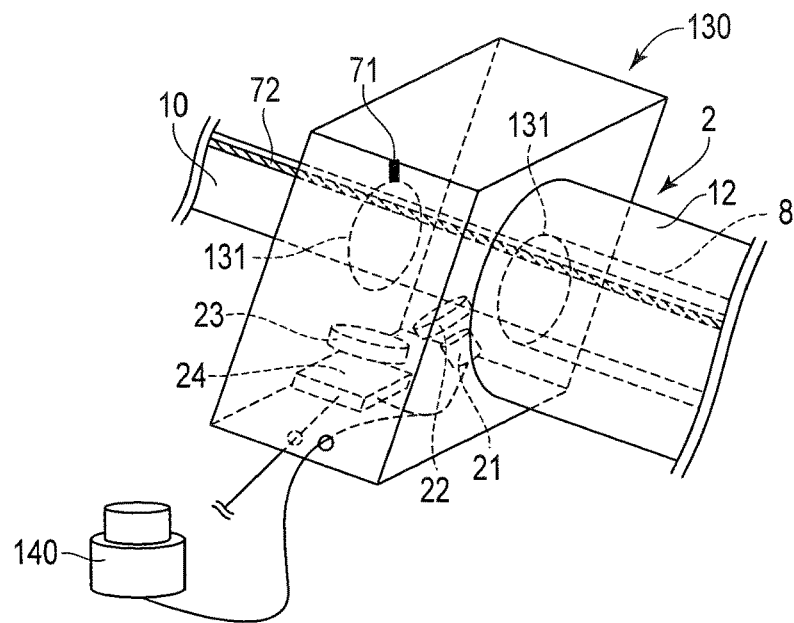
F I G. 9
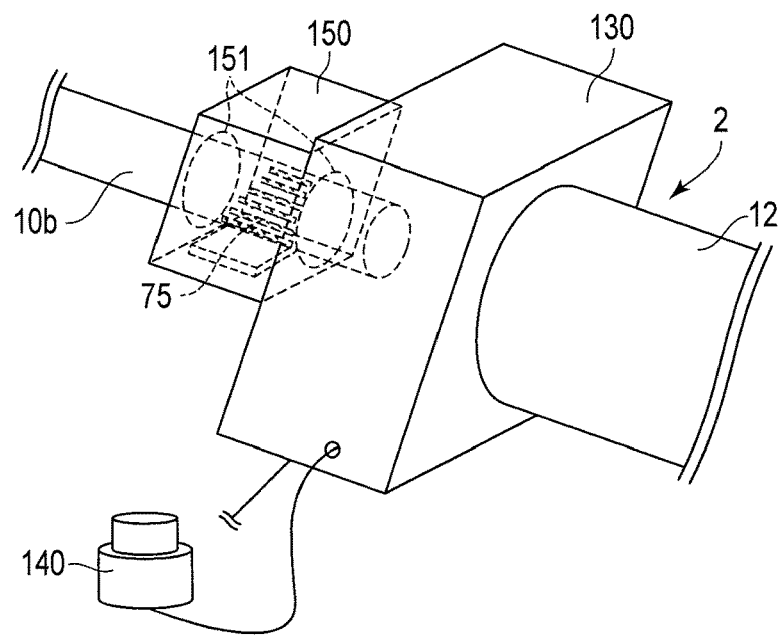
F I G. 10

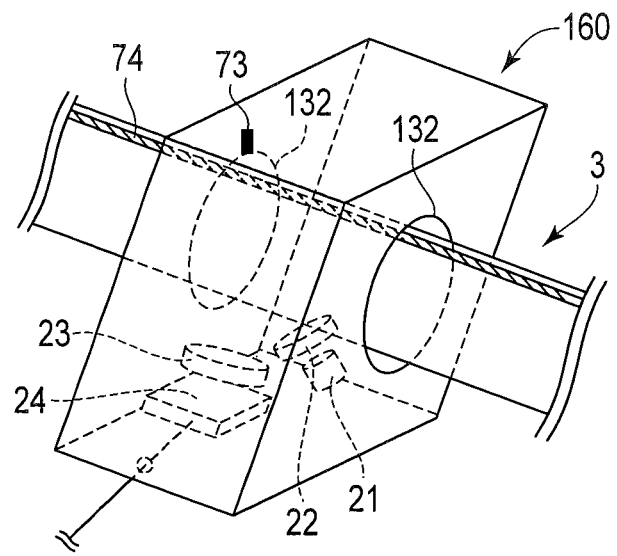
F I G. 12
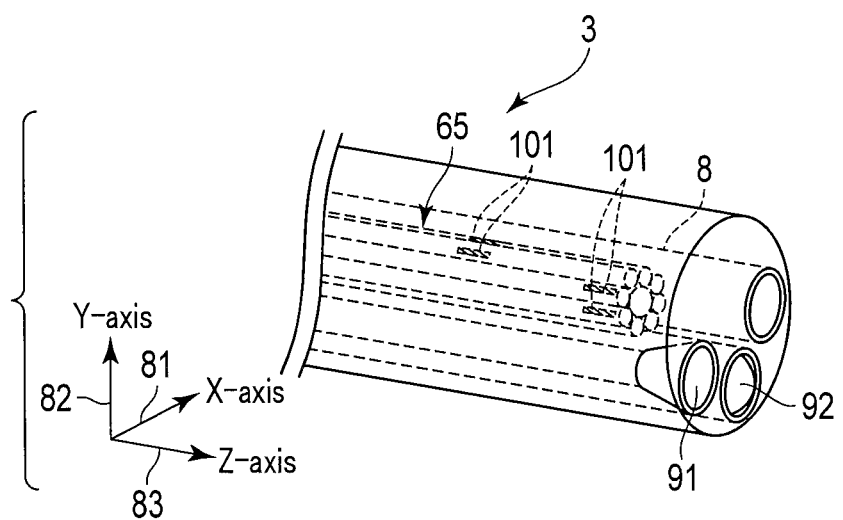
F I G. 13

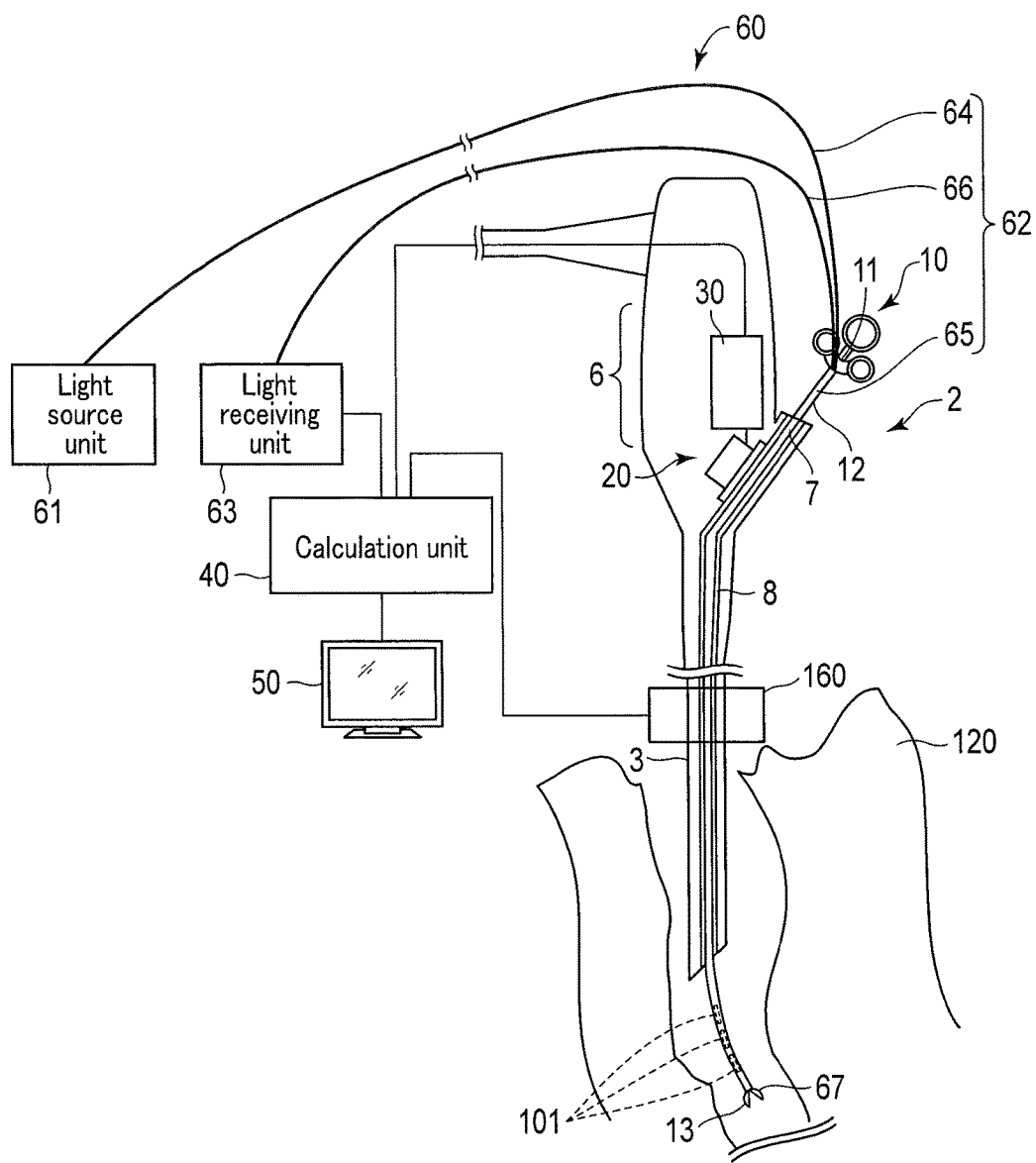
F I G. 16

INSERTION SYSTEM HAVING INSERTION PORTION AND INSERTION MEMBER

CROSS-REFERENCE TO RELATED APPLICATIONS

This is a Continuation Application of PCT Application No. PCT/JP2013/076884, filed Oct. 2, 2013, which was published under PCT Article 21(2) in Japanese.

This application is based upon and claims the benefit of priority from prior the Japanese Patent Application No. 2012-225460, filed Oct. 10, 2012 the entire contents of which are incorporated herein by references.

BACKGROUND OF THE INVENTION

1. Field of the Invention

The present invention relates to an insertion system which detects an insertion amount and a rotation amount of an insertion member to be inserted into a lumen through an insertion portion.

2. Description of the Related Art

In general, an insertion system of an endoscope has an insertion portion to be inserted into an insertion target, an insertion hole to insert at least an insertion member such as a treatment instrument, and an operation portion to curve the insertion portion. The insertion portion is provided with a channel which passes through the insertion portion from the insertion hole to the distal end and through which the insertion member is inserted. The insertion member is, for example, a member in which a treatment portion such as a grasp member or a cutting member is provided at the distal end of a cable member.

As an insertion member, for example, Jpn. Pat. Appln. KOKAI Publication No. 2010-22619 has disclosed a configuration in which at the proximal end (insertion-hole-side end) of a flexible cable, a rotational operation portion for adjusting the direction of the distal end of this cable is provided. This rotational operation portion is frictionally engaged with the outer circumferential portion of the cable of the insertion member. If the rotational operation portion is rotationally operated, rotational force in the direction around the axis of the rotation is transmitted to the cable in the frictionally engaged state, so that the position of the distal end of the insertion member in the direction around the axis can be adjusted by the proximal end of the cable.

In the above-mentioned Jpn. Pat. Appln. KOKAI Publication No. 2010-22619, when the insertion member is inserted in the channel of the insertion portion, it is difficult for an operator to accurately recognize the insertion position of the distal end of the insertion member and its rotational direction around the axis while observing an endoscopic observation image. It is also difficult for the operator to accurately recognize the insertion position of the distal end of the insertion member and its rotational direction around the axis through manual sensation by the operator when the operator has inserted the insertion member in the channel of the insertion portion.

An object of the present invention is to provide an insertion system that makes it possible to accurately recognize the insertion position and direction of an insertion member by detecting operation support information such as an insertion amount and a rotation amount of the insertion member, and the position and shape of the distal end thereof.

BRIEF SUMMARY OF THE INVENTION

According to an embodiment of the present invention, there is provided an insertion system characterized by comprising: an insertion portion including at least a grasp portion, an insertion portion to be inserted into a specimen, and an insertion channel passing from the proximal end of the insertion portion to the distal end thereof; an insertion member to be inserted into the insertion channel; a first state detector which is disposed in the insertion portion and which detects information to calculate at least one of an insertion amount of the inserted insertion member in an insertion direction along a longitudinal direction and a rotation amount of the insertion member around its central axis along the insertion direction; and a calculation unit which calculates, from a detection result by the second shape sensor, operation support information to support in an insertion operation of the insertion member inserted through the insertion channel.

BRIEF DESCRIPTION OF THE SEVERAL VIEWS OF THE DRAWINGS

FIG. 1 is a schematic configuration diagram of the whole insertion system according to a first embodiment;

FIG. 2 is a perspective view of an insertion hole of an insertion channel of an endoscope in the insertion system according to the first embodiment;

FIG. 5 is a schematic configuration diagram showing how the endoscope in the insertion system according to the first embodiment is inserted in a specimen;

FIG. 6A is a perspective view of the distal end of an insertion member in the insertion system according to the first embodiment;

FIG. 6B is a sectional view taken along the line A-A shown in FIG. 6A;

FIG. 9 is a perspective view of a state detector according to the first modification of the first embodiment;

FIG. 10 is a perspective view of a rotation reference position detector according to a second modification of the first embodiment;

FIG. 12 is a perspective view of a state detector in the insertion system according to the second embodiment;

FIG. 13 is a perspective view of the distal end of a flexible insertion portion in the insertion system according to the second embodiment;

FIG. 16 is a schematic configuration diagram of a hard insertion system according to a first modification of the second embodiment;

DETAILED DESCRIPTION OF THE PREFERRED EMBODIMENT

Figure 3:
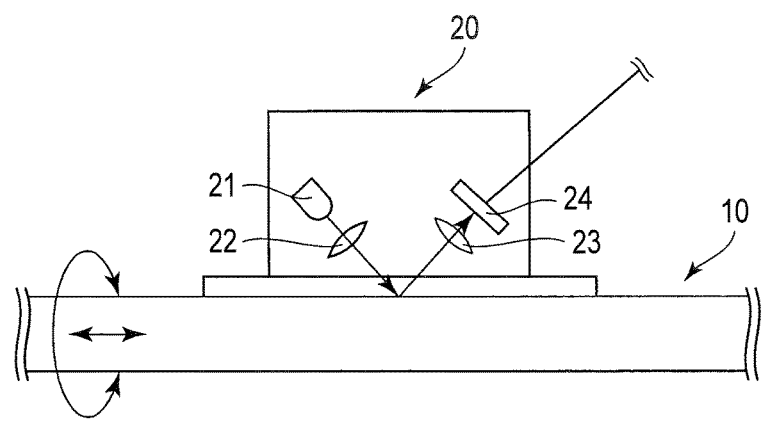
FIG. 3 is a schematic configuration diagram of the main parts of a state detector in the insertion system according to the first embodiment.

Hereinafter, embodiments of the present invention will be described in detail with reference to the drawings.

FIG. 1 shows an insertion system 1 such as an endoscope system according to the first embodiment. The insertion system 1 has at least a flexible insertion portion 2, an insertion member 10 which is inserted through the flexible insertion portion 2, a calculation unit 40 which calculates later-described operation support information, a display unit 50 which displays processed detection data, a shape sensor (first shape sensor) 60 which optically detects the curing state of the insertion member 10, a light source unit 61, and a light receiving unit 63. Here, for example, the flexible insertion portion 2 is a flexible endoscope, and the insertion member 10 generically refers to instruments to be inserted into an insertion channel (so-called forceps opening) of the insertion portion from the outside and typically includes a treatment instrument and a catheter.

Figure 4:
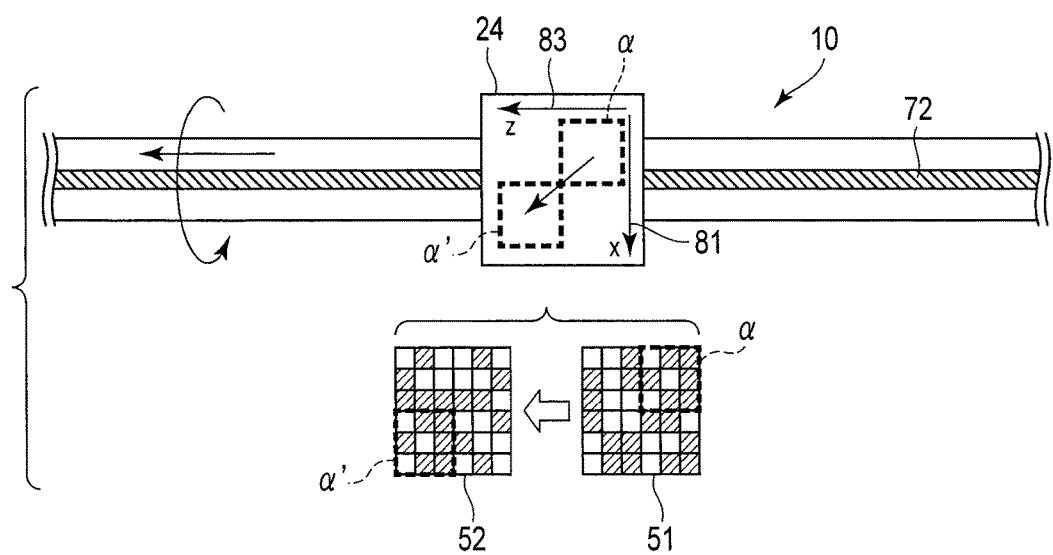
FIG. 4 is an expletory diagram illustrating pattern matching by an optical pattern detector in the insertion system according to the first embodiment.

In the following explanation, one of two axes intersecting in directions that intersect at right angles on a plane that intersects at right angles with the longitudinal direction of the insertion member 10 as shown in FIG. 4 is an x-axis 81, and the other axis is a y-axis 82 (see FIG. 6B). An axis in a direction along the longitudinal direction of the insertion member 10 is a z-axis 83. The operation support information is information which improves operability when operations to change an insertion amount, a rotation amount, and pose of the insertion member 10 or the flexible insertion portion 2, the position or shape of the distal end, or the direction of the distal end are performed. The rotation amount is the amount of rotation around the central axis of the insertion member 10 which is inserted through the flexible insertion portion 2.

The insertion system 1 according to the present embodiment can be easily applied to either a flexible endoscope or a hard endoscope. The flexible insertion portion 2 has at least a flexible elongated insertion portion 3, a distal portion 4 which is disposed at the distal end of the insertion portion 3 and which is made of a hard member, an operation portion 5 for operating the directions of the insertion portion 3 and the distal portion 4, a grasp portion 6 to be grasped by an operator, an insertion hole 7 having an opening to insert the insertion member 10, a state detector (first state detector) 20 which detects the state of the insertion member 10, and a storage unit 30 to store information to correct detected information. Although the distal portion 4 described in the present embodiment is made of a hard material, the distal portion 4 does not always need to be made of a hard material.

An insertion channel 8 which communicates at least from the insertion hole 7 to the distal end of the distal portion 4 is provided inside the insertion portion 3. The end of the insertion portion 3 on the side of the insertion hole 7 is referred to as a proximal end, and the end on the side of the distal portion 4 is referred to as a distal end. The insertion portion 3 may further have an observation unit such as an imaging camera to observe an unshown target.

The state detector 20 detects the position and state (direction) of the insertion member 10 to be inserted into the insertion channel 8. Here, the position and state of the insertion member 10 is estimated from, for example, the insertion amount of the insertion member 10 to be inserted into the insertion channel 8, and the amount of rotation around the central axis of the insertion member 10. The insertion amount of the insertion member 10 is a length from a detection start position which is the open surface of the insertion channel 8 to the distal end of the insertion member 10. The direction of the insertion member 10 is found by the amount of rotation around the axis from the initial condition of the insertion of the insertion member 10.

FIG. 2 is a perspective view of the insertion hole 7 of the insertion channel 8 of the flexible insertion portion 2 which is an endoscope. As shown in FIG. 2, a first mark 71 which is a reference point of the rotation of the insertion member 10 is formed at one point in the circumferential direction in the open surface of the insertion hole 7 viewed from the insertion direction of the insertion member 10.

A linear second mark 72 along the axial direction is formed on the surface of the insertion member 10. During the insertion of the insertion member 10 to be inserted into the insertion channel 8, the direction of the insertion of the insertion member 10 can be defined by adjusting the first mark 71 and the second mark 72 to each other. Here, the position where the first mark 71 and the second mark 72 are adjusted to each other is a reference position of the rotation amount, that is, a position at 0°, and is a first rotation origin (first rotation reference position) to define the insertion direction of the insertion member 10 inserted in the insertion channel 8.

FIG. 3 is a schematic configuration diagram of the state detector 20 of the insertion system 1 according to the present embodiment. This state detector 20 is disposed outside the insertion channel 8. The detection surface of the state detector 20 is disposed in an opening formed in the side surface of the insertion channel 8. Thus, the detection surface of the state detector 20 can detect the surface (outer circumferential surface) of the insertion member 10 to be inserted into the insertion channel 8. Therefore, the state detector 20 can detect information to calculate, for example, an insertion amount and a rotation amount of the insertion member 10.

As shown in FIG. 3, the state detector 20 has at least a light source unit 21 which applies light to the insertion member 10, a projection lens 22 which collects irradiating light from the light source unit 21, a light receiving lens 23 which receives reflected light reflected on the surface of the insertion member 10, and an optical pattern detector 24 which detects the light that has passed through the light receiving lens 23.

The light source unit 21 of the state detector 20 is disposed so that the flux of the irradiating light will be applied to the outer circumferential surface of the insertion member 10 and some of the reflected light reflected on the outer circumferential surface will enter the optical pattern detector 24. The projection lens 22 is placed between the state detection light source unit 21 and the insertion member 10 so that the light emitted from the light source unit 21 of the state detector 20 will be efficiently applied to the outer circumferential surface of the insertion member 10. In the following explanation, the light emitted from the state detection light source unit 21, or a light flux is referred to as light source light.

The light source unit 21 of the state detector 20 is a light source which emits coherent light as the light source light, and is, for example, an LED or a laser light source. In the present embodiment, the light source unit 21 is described as the laser light source.

The coherent light has a phase correlation, and can therefore produce a clear phase difference in the reflected light even if the surface of an object to which the coherent light is applied is slightly irregular. The use of the coherent light when applied to, for example, a glossy smooth surface permits clear image data regarding the smooth surface to be acquired. That is, when the coherent light is used, information regarding the outer circumferential surface of the insertion member 10 can be acquired as a clear optical pattern. The optical pattern is, for example, a speckle pattern.

The light receiving lens 23 is disposed between the optical pattern detector 24 and the insertion member 10 so that the light source light reflected on the outer circumferential surface of the insertion member 10 will be focused on the light receiving surface of the optical pattern detector 24.

As shown in FIG. 4, the optical pattern detector 24 has, for example, an imaging device in which light receiving elements are arrayed in matrix form. The imaging device is, for example, a CCD or a C-MOS image sensor.

The optical pattern detector 24 has at least a function of successively imaging a smooth surface having a curvature and acquiring, as image data, information regarding an optical pattern included in the obtained image, a function of detecting that the distal end of the insertion member 10 has entered a detectable range, and a (detection start position correcting) function of permitting any detection start position to be determined within the detectable range. That is, the optical pattern detector 24 starts imaging when the distal end of the insertion member 10 has entered the detectable range, successively images an imaging range including a predetermined optical pattern on the outer circumferential surface of the insertion member 10, and acquires the optical pattern as image data. Whether the optical pattern detector 24 performs processing is not limited by the surface shape. That is, the surface may be an irregular plane. The optical pattern detector 24 can detect image data at detection times $t0, t1, t2, \ldots$, and to with given time intervals, or at properly set successive detection times.

The optical pattern detector 24 uses one of the obtained images (image data) as a reference image to set a given optical pattern present in the image as a reference pattern. Further, an optical pattern corresponding to the reference pattern is detected from an image acquired after a predetermined length of time has elapsed. A so-called pattern matching function is provided to then calculate a displacement amount between the reference pattern and the corresponding optical pattern in the image. Here, any range of the optical patterns to be detected can be set.

A calculating method of each direction displacement amount of the optical pattern detector 24 is described with reference to FIG. 4. As shown in FIG. 4, the optical pattern detector 24 compares image data 51 obtained at a given time $tn-1$ with image data 52 obtained at the time to after a given length of time has elapsed since the time $tn-1$. At the same time, displacements on the image data are compared between any reference pattern $\alpha$ selected from the image patterns present in the image of the image data 51 and an optical pattern $\alpha'$ corresponding to the reference pattern $\alpha$ present in part of the image pattern present in an image of the image data 52, and displacement amounts of the direction of the x-axis 81 which is a rotational direction and the direction of the z-axis 83 which is an insertion direction are calculated. Therefore, the optical pattern detector 24 can integrate the displacement amounts of the reference pattern at any successive times. A calculated displacement amount on the image is output to the calculation unit 40.

Now, the insertion member 10 is described with reference to FIG. 5. In this insertion member 10, an operation portion 11 which is operated by a user is disposed at the proximal end of a cable-shaped member (cable member) 12. A distal member 13 to conduct a treatment such as grasping or cutting is disposed at the distal end of the cable member 12. Moreover, for example, the insertion member 10 is provided with reflective optical fiber sensors as shape sensors (first shape sensors) 60 for detecting the shape (curing state) of the insertion member 10.

An operation wire 14 is inserted through the cable member 12, and the shape sensors 60 are disposed in the cable member 12. A cover member 15 is provided on the outer circumferential portion of the cable member 12. On the outer circumferential surface of the cover member 15 of the cable member 12, the above-mentioned second mark 72 to define an insertion direction extends along the axial direction.

The operation wire 14 is disposed through a shaft center space of the cable member 12. The distal side of the operation wire 14 is coupled to the distal member 13, and the proximal side thereof is coupled to the operation portion 11. In response to the operation of the operation portion 11, the operation wire 14 moves back and forth in the axial direction, and the distal member 13 opens and closes accordingly. The distal member 13 has, for example, a function of grasping or cutting a target at a desired position inside a specimen 120.

The shape sensor 60 has a shape sensor light source unit 61 which emits light, optical fiber bundles 62 which are bundles of optical fibers, and a shape sensor light receiving portion 63. Here, each of the optical fiber bundles 62 has a light supply optical fiber bundle portion 64, a detection light optical fiber bundle portion 65, and a light receiving optical fiber bundle portion 66.

One end side of the light supply optical fiber bundle portion 64 is coupled to the light source unit 61. One end side of the light receiving optical fiber bundle portion 66 is coupled to the light receiving portion 63. Each of the other end sides of the light supply optical fiber bundle portion 64 and the light receiving optical fiber bundle portion 66 is coupled to the detection light optical fiber bundle portion 65. Here, a coupling portion which constitutes a Y-shape to split light into a guide-in path and a guide-out path is provided in a junction (not shown) between the other end sides of the light supply optical fiber bundle portion 64 and the light receiving optical fiber bundle portion 66 and the detection light optical fiber bundle portion 65.

The detection light optical fiber bundle portion 65 has detection optical fibers disposed inside the cable member 12. In the present embodiment, as shown in FIG. 6B, eight optical fibers comprising four optical fibers 65a and four optical fibers 65b are shown by way of example. These detection optical fibers 65a and 65b are disposed around the operation wire 14 in the shape of a ring. Each of the detection optical fibers 65a (65b) has a reflecting portion 67 at the distal end, and an optical characteristic converting portion 101 at a position to detect the curving of the cable member 12 between the reflecting portion 67 and the junction. Here, the position to detect the curving of the cable member 12 is, for example, the position where the distal end of the cable member 12 curves in the longitudinal direction.

Each of the optical fibers 65a (65b) comprises at least a core, and cladding that encloses the core. A cover member may be further formed on the outer circumference of the cladding. The optical characteristic converting portion 101 has a function of converting the characteristics of the light guided through the core of each of the optical fibers 65a (65b). The optical characteristic converting portion 101 is, for example, a light guide loss portion or a wavelength converting portion. For example, the light guide loss portion includes a light absorber, and the wavelength converting portion includes a fluorescent material. The optical characteristic converting portion 101 is configured to be applied to the part of each of the optical fibers 65a (65b) where the cladding is removed and the core is exposed. The optical characteristic converting portion 101 may be an opening formed so that the light guided through the core of the optical fiber 65a (65b) will leak out.

The optical characteristic converting portions 101 are formed so that the amount of light converted at the location to recognize the curving direction of the cable member 12 will vary. If each of the optical characteristic converting portions 101 can accurately recognize the curving direction, the amount of light produced as a result of conversion may be the same. For example, the optical characteristic converting portions 101 may be formed so that the number of opening directions in the vertical direction may be different from that in the horizontal direction in the cable member 12.

The detection optical fiber bundle portions 65 are applied so that at least two detection optical fibers 65a and 65b make a pair of sensors to detect the curving of the cable member 12 in two directions, that is, the curving in the direction of the x-axis 81 and the curving in the direction of the y-axis 82. That is, as shown in FIG. 6A, in the longitudinal direction of the cable member 12, the detection optical fiber 65a having the optical characteristic converting portion 101 which is open in the direction of the x-axis 81 and the detection optical fiber 65b having the optical characteristic converting portion 101 which is open in the direction of the y-axis 82 are disposed at one detection position.

The light emitted from the light source unit 61 is then guided to the junction through the light supply optical fiber bundle portion 64, and guided to each of the optical fibers 65a (65b) of the detection optical fiber bundle portion 65. The light guided to each of the optical fibers 65a (65b) is guided to the distal end of each of the optical fibers 65a (65b), and reflected toward the junction by the reflecting portion 67.

Furthermore, the reflected light from the reflecting portion 67 of each of the optical fibers 65a (65b) is split at the junction, and enters the light receiving optical fiber bundle portion 66. The light guided from the eight detection optical fibers 65a (65b) is guided to the shape sensor light receiving portion 63 through the light receiving optical fiber bundle portion 66. At the same time, the shape sensor light receiving portion 63 can independently detect the amount of received light by the respective detection optical fibers 65a (65b).

The shape sensor light receiving portion 63 is electrically connected to the calculation unit 40 by, for example, a cable. The shape sensor light receiving portion 63 then generates data regarding each detected amount of light guided from the eight detection optical fibers 65a (65b).

The calculation unit 40 has the storage unit 30. This storage unit 30 individually prestores characteristics (correction values) regarding flexible insertion portions 2 of endoscopes. The correction value of the insertion amount is stored for each type of the endoscope because the length of the endoscope insertion portion varies or the location of the insertion portion state detector 20 varies depending on the type of endoscope. Here, the correction value is the distance from the detection start position of the state detector 20 to the distal end of the insertion portion 3. This value is necessary to calculate the amount (net insertion amount) in which the insertion member 10 is actually inserted in the specimen 120 through the insertion channel 8 of the insertion portion 3. This correction value of the insertion amount stored in the storage unit 30 is output to the calculation unit 40. For the storage unit 30, a memory attached to a computational processing circuit in the calculation unit 40 may be used.

The calculation unit 40 has a function of correcting information to calculate the insertion amount and rotation amount detected by the shape sensor 60, and calculating desired operation support information. Here, the desired operation support information means that any information which permits operation support information to be acquired can be determined. For example, the desired operation support information is the distance (insertion amount) from the detection position of the state detector 20 to the distal end of the insertion member 10. The desired operation support information is also the shape of the insertion member 10 in this case.

Moreover, the desired operation support information may also be the shape of the insertion portion 3 in the case where the distance from the distal end of the insertion portion 3 to the distal end of the insertion member 10 is an insertion amount. The calculation unit 40 can calculate the position and shape of not only the distal end but also a desired part. For example, the calculation unit 40 can calculate the position and shape of any part of the insertion member 10 inserted in the specimen 120.

In the process of calculating an insertion amount and a rotation amount from the displacement amount of the reference pattern on the above-mentioned image data in the calculation unit 40, a coefficient of each direction to convert from the displacement amount of the reference pattern on the image data to the insertion amount and the rotation amount is found in advance.

The coefficient of each direction is multiplied by each of coefficients $a_f$ and $b_f$ that take into consideration the above-mentioned various correction values of the insertion portion 3 stored in the storage unit 30, and an insertion amount $m_{f0}$ and a rotation amount $\theta_{f0}$ are thereby calculated. Here, the insertion amount $m_{f0}$ is the amount of insertion from the detection start position of the state detector 20 relative to the flexible insertion portion 2. The rotation amount $\theta_{f0}$ is the rotation amount of the insertion member 10 relative to the flexible insertion portion 2 with respect to the first rotation reference position where the above-mentioned first and second marks 71 and 72 are adjusted to each other. An insertion amount $m_{f1}$ (net insertion amount) which is the distance from the distal end of the insertion portion 3 to the distal end of the insertion member 10 is calculated from the difference between a correction value $L_f$ which is the distance between the detection start position and the distal end of the insertion portion 3 found by the state detector 20, and the insertion amount $m_{f0}$ of the insertion member 10.

An expression that shows the relation between the change amount of the light amount detected by the shape sensor 60 and the curving amount of the insertion member 10 is found in advance. Therefore, the curving amount of the insertion member 10 is calculated from the light amount of the shape sensor 60.

A calculation result of a desired direction can be selectively output. Equation 1 which is a computational expression of the insertion amount of the insertion member 10, Equation 2 which is a computational expression of the rotation amount, Equation 3 which is a computational expression of the insertion amount $m_{f1}$ from the distal end of the insertion portion 3, and Equation 4 which is a computational expression of a curving amount $\Phi_f$ of a curved portion of the insertion member 10 are shown below. That is, the calculation unit 40 repeats the above-mentioned processing, and integrates the displacement amounts of the coordinates of given successive detection times, and thereby calculates an insertion amount and a rotation amount of the insertion member 10 from a given detection time to the desired detection time.

$$m_{f0}=a_f \times \Delta z \tag{1}$$

wherein $m_{f0}$ is the insertion amount from the time $t_{n-1}$ to the time $t_n$, $\Delta z$ is a coordinate difference in the direction of the z-axis 83 regarding the pattern to which the image data from the time $t_{n-1}$ to the time $t_n$ corresponds, and $a_f$ is an insertion amount conversion coefficient.

$$\theta_{f0}=b_f \times \Delta X \tag{2}$$

wherein $\theta_{f0}$ is the rotation amount from the time $t_{n-1}$ to the time $t_n$, $\Delta x$ is a coordinate difference in the direction of the x-axis 81 regarding the pattern to which the image data from the time $t_{n-1}$ to the time $t_n$ corresponds, and $b_f$ is a rotation amount conversion coefficient.

The calculated insertion amount $m_{f0}$ is a movement amount from the time $t_0$ at which the state detector 20 has started detection to a given time $t_n$. The net insertion amount $m_{f1}$ is calculated by the difference between the calculated insertion amount $m_{f0}$ and the correction value $L_f$.

$$m_{f1}=m_{f0}-L_f \tag{3}$$

wherein $L_f$ is the correction value of the insertion amount of the insertion member, $m_{f0}$ is the insertion amount from the time $t_{n-1}$ to the time $t_n$, and $m_{f1}$ is the net insertion amount.

The calculation unit 40 can also calculate the curving amount $\Phi_f$ of the curved portion of the insertion member 10. The curving amount $\Phi_f$ of a curve detector is calculated by the use of a change $\Delta l_f$ in the light transmission amount of the shape sensor 60.

$$\Phi_f=f(\Delta l_f) \tag{4}$$

wherein $\Phi_f$ is the curving amount of the curved portion of the insertion member 10, and $\Delta l_f$ is the change in the light transmission amount.

In the present embodiment, after the insertion portion 3 is inserted into a desired position inside the specimen 120, the insertion member 10 is inserted into the specimen 120 from the insertion hole 7 through the insertion channel 8. If the detection of the insertion amount is started when the distal end of the insertion member 10 has entered the detectable range of the optical pattern detector 24, the light source light is applied to the outer circumferential surface of the insertion member 10 from the state detection light source unit 21. The applied light source light is reflected by the outer circumferential surface, and some of the reflected light enters the optical pattern detector 24.

The optical pattern detector 24 images the optical pattern from the detection start time $t_0$ at given time intervals, and outputs the images as image data. In this instance, image data are successively acquired at given detection times $t_1$, $t_2$, ..., $t_n$, .... The optical pattern detector 24 determines at least one reference pattern present in the image of the image data acquired at the given detection time from the acquired image data, and detects an optical pattern that corresponds to the reference pattern from the images of the image data after a predetermined time has elapsed since the detection time. A displacement amount calculation unit calculates displacement amounts in the directions following the x-axis 81 which is the rotational direction and the z-axis 83 which is the insertion direction from the displacement of the optical pattern relative to the reference pattern.

Similarly, calculation processing is performed for each displacement amount at each interval, for example, a given time interval between the time $t_1$ and the time $t_2$, between the time $t_2$ and the time $t_3$, or between the time $t_{n-1}$ and the time $t_n$. Amounts of displacement relative to the reference pattern at these time intervals are then integrated, and, for example, a movement amount and a rotation amount of the insertion member 10 from the position of the detection time $t_0$ at which the detection has started to the position of the time $t_n$ at which the detection has ended. Amounts at the given time interval can also be calculated as the movement amount and the rotation amount of the insertion member 10.

The information regarding the detection start position in the optical pattern detector 24 and the calculated displacement amount in each direction are sent to the calculation unit 40.

At the same time, the storage unit 30 sends, to the calculation unit 40, information regarding the distance from the location of the detector 20 applied to the recorded detection to the distal end of the insertion portion 3.

When the insertion member 10 extending from the distal end of the insertion portion 3 is curved, the amount (light transmission amount) of light received by the shape sensor light receiving portion 63 is changed by the optical characteristic converting portion 101 disposed at a predetermined position. This light transmission amount is sent to the calculation unit 40.

The calculation unit 40 receives the information sent from the state detector 20, the storage unit 30, and the shape sensor 60, and calculates operation support information for the insertion member 10 from the above information. The display unit 50 displays the operation support information calculated by the calculation unit 40.

According to the present embodiment, the state detector 20 is disposed in the vicinity of the channel 8 of the flexible insertion portion 2, so that the insertion amount and rotation amount of the insertion member 10 relative to the flexible insertion portion 2 can be calculated. The image displayed on the display unit 50 is visually recognized, and the insertion amount and rotation amount of the insertion member 10 can be quantitatively recognized, so that the operability of the insertion member 10 improves.

Since the state detector 20 is disposed in the vicinity of the channel 8 of the grasp portion 6, the state detector 20 can be disposed without changing the diameter of the insertion portion 3. Thus, the insertion portion 3 and the insertion member 10 can be easily inserted into the specimen 120.

Since the state detector 20 is disposed in the grasp portion 6 having a relatively large internal space, the restriction on the size of the state detector 20 is eased. Since the state detector 20 is disposed in the vicinity of the channel 8 of the grasp portion 6, the state detector 20 can easily detect the flexible insertion portion 2.

The calculation unit 40 calculates the operation support information, and the insertion member 10 can thus be operated in accordance with the operation support information, so that the operability of the insertion member 10 improves. That is, the operation support information for the insertion member 10 outside the imageable range of the imaging camera of the insertion portion 3 can be obtained, so that the operability can be further improved.

Since the correction values of the insertion portions 3 of the flexible insertion portions 2 are prestored in the storage unit 30, the state detector 20 acquires the operation support information in the flexible insertion portions 2 having different specifications, and can therefore be used for general purpose.

As described above, the flexible insertion portion 2 has the first mark 71 provided at the end of the insertion hole 7 of the insertion channel 8. Therefore, if the first mark 71 is aligned with the second mark 72 formed on the outer circumferential surface of the cable member 12 of the insertion member 10, the insertion member 10 can be easily adjusted to the rotation reference position.

The optical pattern detector 24 of the state detector 20 can simultaneously detect displacement amounts in the insertion direction (the direction of the z-axis 83) and the rotation direction (the direction of the x-axis 81) by optical pattern matching, so that the displacement amounts in two directions can be detected by one detector.

Although the state detector 20 detects the displacement amount in each direction by the optical pattern detector 24 in the configuration according to the present embodiment, a calculation unit may be further provided to generate or convert information to calculate the insertion amount and rotation amount of the insertion member 10 from the displacement amount in each direction of the reference pattern in the image data.

Figure 7:
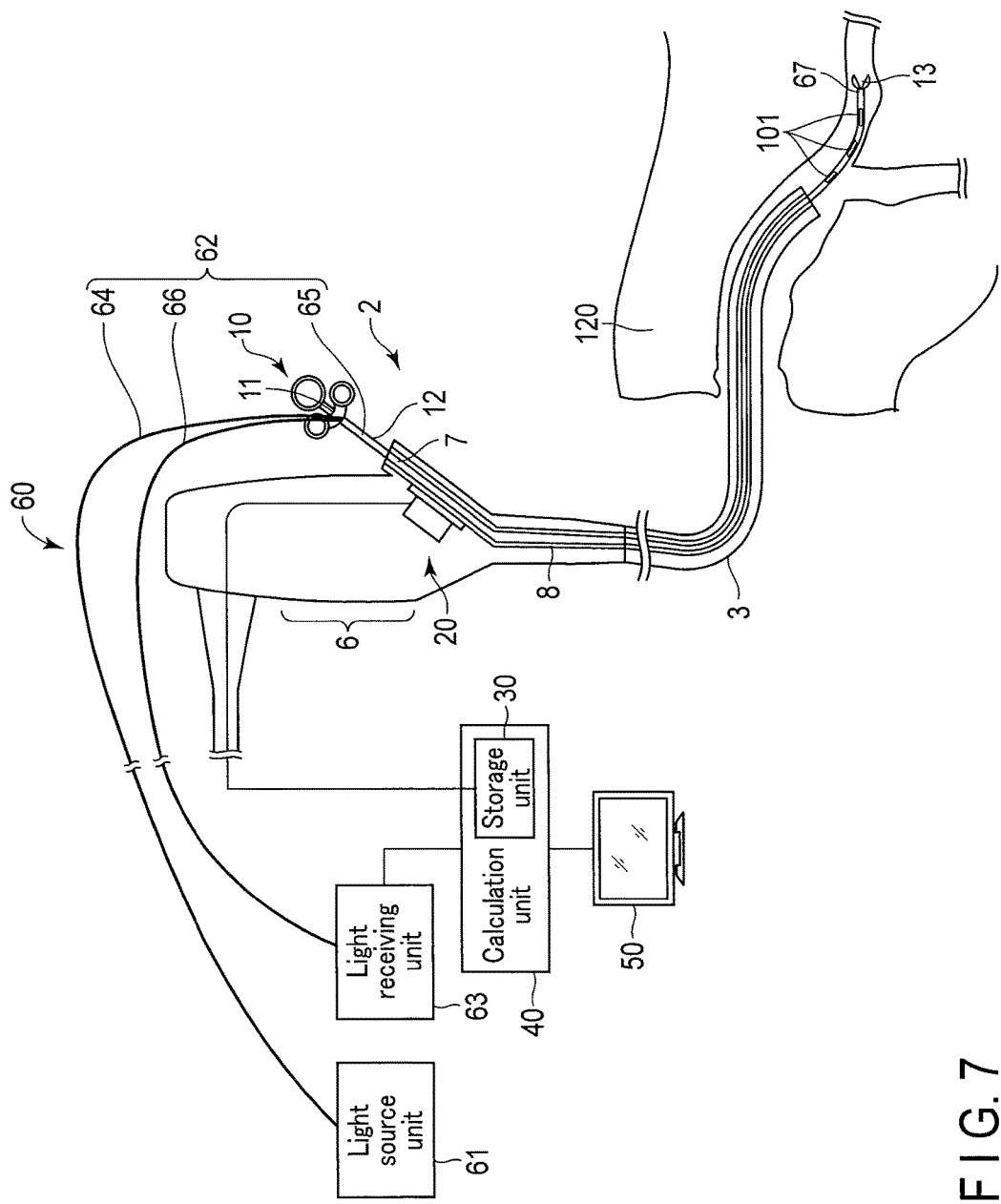
FIG. 7 is a schematic configuration diagram showing a modification of a flexible insertion system in which a calculation unit and a storage unit in the insertion system according to the first embodiment are integrated.

As in a modification shown in FIG. 7, the storage unit 30 may be incorporated in the calculation unit 40. The calculation unit 40 can calculate the operation support information from the information stored in the storage unit 30 provided therein and from the information regarding the position of the distal end of the insertion member 10 and the shape of the insertion member 10 acquired from the state detector 20.

Figure 8:
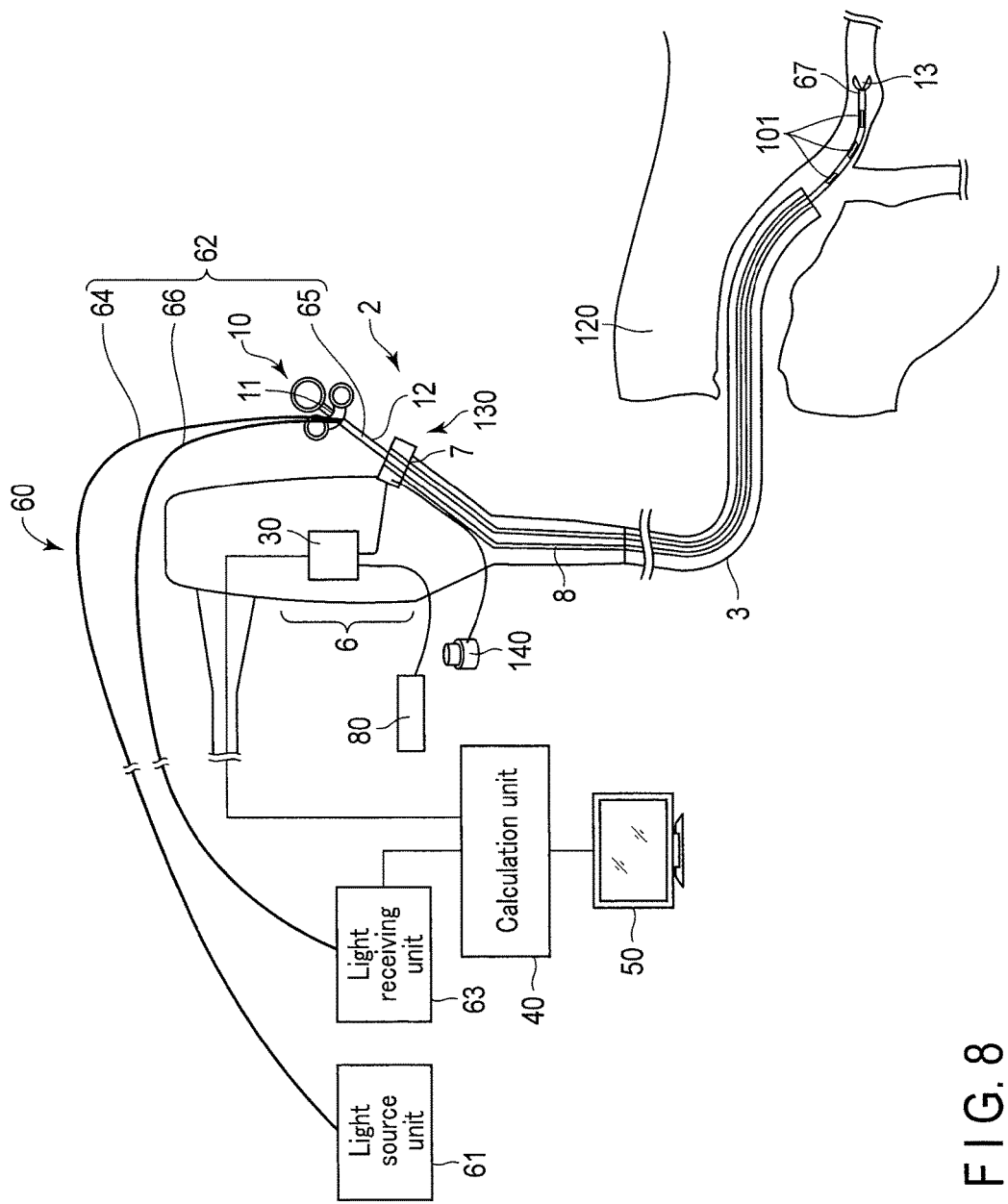
FIG. 8 is a schematic configuration diagram showing an insertion system according to a first modification of the first embodiment.
Figure 11:
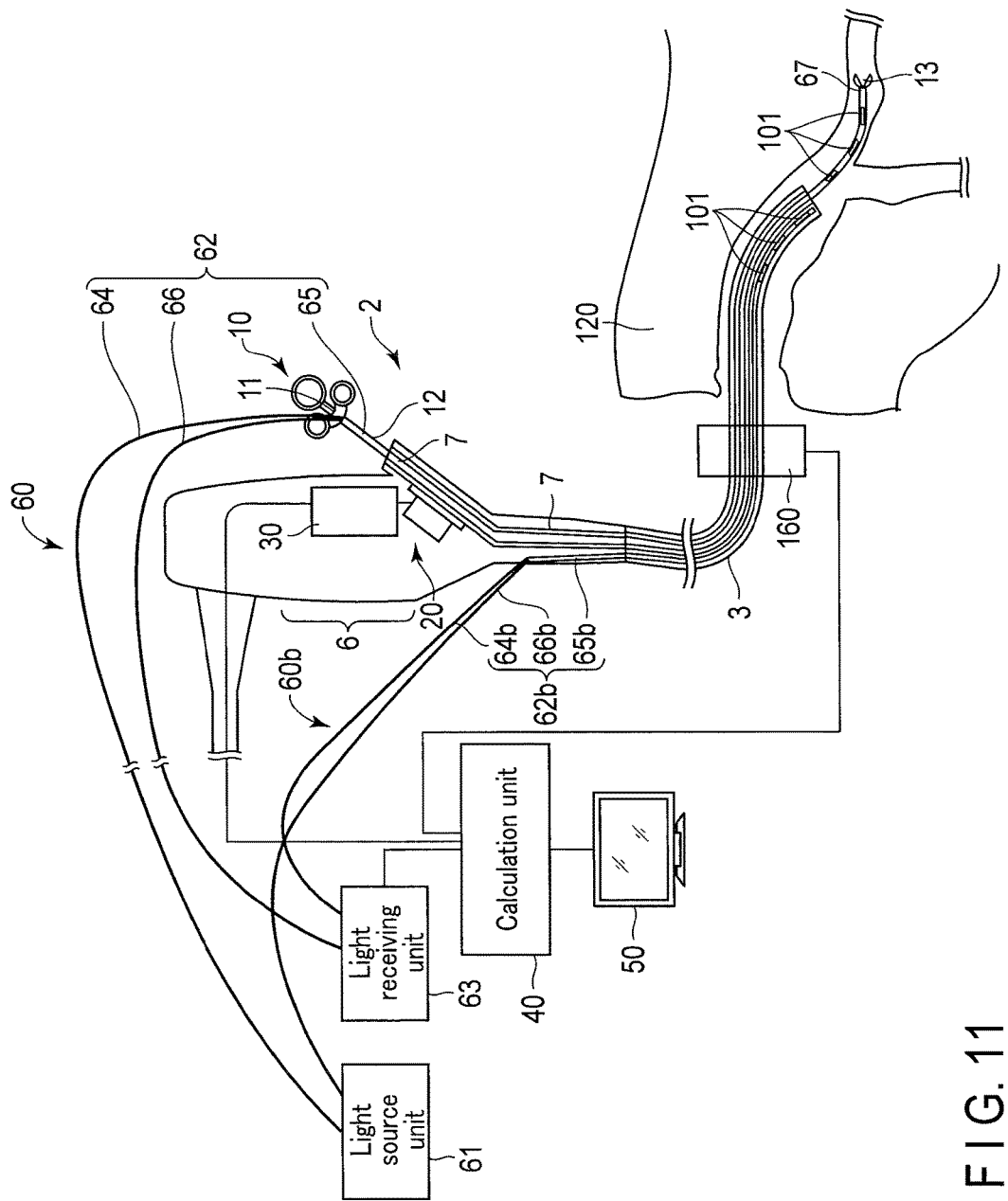
FIG. 11 is a schematic configuration diagram of an insertion system according to a second embodiment.

A first modification of the first embodiment is described with reference to FIG. 8 and FIG. 9.

The configuration of the insertion system 1 according to the first modification is substantially equivalent to the configuration of the insertion system 1 according to the first embodiment, but the configuration of a state detector (first state detector) 130 is different. Components in FIG. 8 equivalent to those in the first embodiment are provided with the same reference signs, and are not described in detail.

FIG. 9 shows a configuration example of the state detector 130 according to the present modification. This state detector 130 is detachably disposed at the distal end of the insertion hole 7. The state detector 130 may be fixed to the distal end of the insertion hole 7.

Although the state detector 130 has a configuration substantially equivalent to that of the state detector 20 according to the first embodiment, this state detector 130 is different in that it is detachably disposed at an opening end of the insertion hole 7 of the insertion channel 8. A bore (opening) 131 through which the insertion member 10 is inserted is formed in the state detector 130. This bore 131 is disposed coaxially with the opening of the insertion hole 7 of the insertion channel 8. The first mark 71 is formed in part of the circumference of the bore 131 in the end face of the state detector 130 on the insertion hole side. This first mark 71 is aligned with the second mark 72 formed on the outer circumferential surface of the cable member 12 to define the rotation reference position. Moreover, the state detector 130 has an input unit 80 (see FIG. 8) to input information regarding the flexible insertion portion 2 to the storage unit 30, and a switch 140 to set a reference time for detection. The switch 140 is connected to, for example, the optical pattern detector 24 and the state detection light source unit 21. The input unit 80 has a function of inputting information to be newly recorded in the storage unit 30.

When pressed, the switch 140 sends a signal to start information detection to the state detector 130. The information detected by this signal is information for calculating an insertion amount and a rotation amount with respect to the insertion position of the insertion member 10. For example, as shown in FIG. 8, the switch 140 is pressed when it is confirmed by an imaging camera provided in the insertion portion 2, X-rays, or a CT image (not shown) that the insertion member 10 has approached a branch in the specimen 120. At the same time, detections (first detection, second detection, . . . , and n-th detection) of information to calculate an insertion amount and a rotation amount with respect to the insertion position of the insertion member 10 at which the switch 140 is pressed are started. Here, n indicates the number of times the switch 140 has been pressed. The detection which is started in accordance with the number of times the switch 140 is pressed is hereinafter referred to as the n-th detection.

In the first modification of the present embodiment, information regarding the location of the state detector 130 and the flexible insertion portion 2 is additionally input to the storage unit 30 from the input unit 80.

At the time of the insertion of the insertion member 10, the first mark 71 and the second mark 72 are adjusted to each other, and are thereby aligned with the rotation reference position. In this condition, the insertion member 10 is inserted into the insertion channel 8, and inserted into the specimen 120. The n-th detection is started by the pressing of the switch 140 when the insertion member 10 has reached a desired position of the specimen 120. This n-th detection is performed simultaneously with the detections based on different insertion positions of the insertion member 10.

The rotation amount and the insertion amount detected in the n-th detection are sent to the calculation unit 40, and output to the display unit 50 as the operation support information based on the insertion position of the insertion member 10 at which the switch 140 has been pressed. At the same time, one or more n-th detection results to be output are selected and output.

According to the present modification, the state detector 130 is detachably disposed at the distal end of the insertion hole 7, and is therefore easily attached and removed. Since the information regarding the flexible insertion portion 2 can be additionally input to the storage unit 30 by the input unit 80, the state detector 130 can be applied for general purpose regardless of the kind of flexible insertion portion 2.

Now, a second modification of the first embodiment is described with reference to FIG. 10.

The configuration of the insertion system 1 according to the second modification is substantially equivalent to the configuration of the insertion system 1 according to the first modification of the first embodiment. Components in FIG. 8 equivalent to those in the first modification are provided with the same reference signs, and are not described in detail. Differences are described. In the insertion system 1 according to the present modification, an insertion member 10b has an optical index (first rotation index) 75 to be an index of rotation on the outer circumferential surface of the distal end. The optical index 75 includes, for example, lines different in length provided in parallel along the circumference of the insertion member 10b. The optical index 75 may be a design having a different shape instead of the lines as long as the rotation amount of the insertion member 10b can be determined.

The state detector 130 has a rotation amount detector (first rotation reference position detector) 150 detachably disposed in the opening end which is in communication with the insertion hole 7 of the insertion channel 8. The rotation reference position detector 150 according to the present modification has a bore (opening) 151 which is disposed coaxially with the bore 131 of the state detector 130 and into which the insertion member 10 is inserted. The bore 151 of the rotation reference position detector 150 is in communication with the bore 131 of the state detector 130.

The rotation reference position detector 150 has, for example, a light receiving element. This rotation reference position detector 150 detects lines of different lengths of the optical index 75 of the insertion member 10b at the time of the insertion of the insertion member 10, and defines a rotation reference position in accordance with the detected shape (the length of the lines).

The calculation unit 40 calculates a substantial rotation amount of the insertion member 10b relative to the flexible insertion portion 2 from the rotation reference position defined by the rotation reference position detector 150 and from the detection result (a displacement amount or a rotation amount) by the state detector 130. In the present modification, the optical index 75 is detected by the rotation reference position detector 150 when the insertion member 10b is inserted into the rotation reference position detector 150. At the same time, the length of the line of the optical index 75 is detected, and the position of the detected length of the line is defined as the rotation reference position. Information regarding the rotation reference position defined by the rotation reference position detector 150 is sent to the calculation unit 40. The calculation unit 40 calculates a rotation amount of the insertion member 10b from the rotation reference position defined by the rotation reference position detector 150 and from the detection result by the insertion portion state detector 130. The calculated result is sent to and displayed on the display unit 50.

According to the second modification, a rotation amount can be calculated from the rotation reference position of the insertion member 10b without alignment, so that the insertion member 10b can be easily inserted. The rotation reference position is mechanically defined, and the rotation amount of the insertion member 10b is calculated, so that more accurate operation support information can be acquired.

In the second modification, the state detector 130 may be integrated with the rotation reference position detector 150. For example, the state detector 130 may have a function of being able to detect the amount of rotation from the rotation reference position by the optical index 75 at the time of the insertion of the insertion member 10b.

In the embodiment described above, the optical fiber bundle 62 may be a single optical fiber in which the optical characteristic converting portion 101 is formed at a predetermined position. For example, the optical characteristic converting portion 101 only converts the wavelength range of particular light. If the optical characteristic converting portions 101 are disposed at several positions at which the curving (deformation) of the insertion member 10 is to be detected, curving of even a single optical fiber at more than one position can be determined. The shape sensor 60 may be some other sensor instead of the optical fiber sensor as long as this sensor can detect shapes.

Although the flexible insertion portion 2 having the state detector 20 and the shape sensor 60 are shown by way of example in the embodiment described above, the flexible insertion portion 2 may only have the state detector 20 and may be configured to only detect the insertion amount of the insertion member 10b.

Although the state detector 20 detects the information to calculate an insertion amount and a rotation amount of the insertion member 10b in the embodiment described above, there may be an insertion sensor to detect the insertion amount of the insertion member 10b, and a rotation sensor to detect the rotation amount of the insertion member 10b.

Moreover, in the embodiment described above, the insertion member 10b is a member to grasp and cut, for example, tissue. However, the insertion member 10b may be, for example, a member only for observation or sensing, or a member with which a catheter treatment is not conducted as long as this member is a cable-shaped member that can be inserted into the insertion channel 8.

Second Embodiment

FIG. 11 to FIG. 15 show a configuration example of the insertion system 1 according to the second embodiment. The flexible insertion system 1 according to the second embodiment is described with reference to FIG. 11. The configuration of the insertion system 1 according to the second embodiment is substantially equivalent to the configuration of the insertion system 1 according to the first embodiment. Therefore, the same components as those in the first embodiment are provided with the same reference signs, and are not described in detail.

The insertion system 1 according to the present embodiment is different from the insertion system 1 according to the first embodiment in the configurations of a state detector 160 and the flexible insertion portion 2. The flexible insertion portion 2 according to the present embodiment has a shape sensor 60b (second shape sensor) which is an optical fiber sensor disposed to detect the curving state of the insertion portion 3. The shape sensor 60b has a configuration substantially equivalent to that of the shape sensor 60, but is provided with a different reference sign to be distinguished from the shape sensor 60.

The state detector (second state detector) 160 according to the present embodiment to detect information for calculating an insertion amount and a rotation amount of the insertion portion 3 is described with reference to FIG. 12.

The state detector 160 according to the present embodiment is a component substantially equivalent to the state detector 130 according to Modification 1 of the first embodiment, but is different in, for example, size and location. For example, the state detector 160 is disposed in the vicinity of the entrance of the specimen 120. The state detector 160 has a bore (opening) 132 having a diameter through which the insertion portion 3 can be inserted. A third mark 73 is provided in part of the circumference of the bore 132 in the side surface of the state detector 160 on the insertion hole side.

The insertion portion 3 has a fourth mark 74 linearly formed along the axial direction of the insertion portion 3 on the outer circumferential surface for visual recognition of an insertion position. When the insertion portion 3 is inserted into the bore 132 of the insertion hole of the state detector 160, the third mark 73 is aligned with the fourth mark 74 to define the reference (second rotation reference position) of the rotation of the insertion portion 3. Here, since the state detector 160 is disposed in the specimen 120, the rotation amount of the insertion portion 3 relative to the third mark 73, that is, the second rotation reference position is substantially the rotation amount of the insertion portion 3 relative to the specimen 120. When the insertion portion 3 is inserted into the bore 132, the state detector 160 detects information to calculate an insertion amount and a rotation amount in the same manner as the state detector 130. The detected information is sent to the calculation unit 40.

In the following explanation, the state detector which detects the state (pose) of the insertion portion 3 is referred to as a second state detector.

The flexible insertion portion 2 and the insertion portion 3 are described with reference to FIG. 13.

The flexible insertion portion 2 is disposed in the insertion portion 3 so that the detection optical fiber bundle portion 65 of the second shape sensor 60b is provided in parallel with the insertion channel 8 of the insertion portion 3. In the flexible insertion portion 2, an illumination device 91 for applying illumination light to a target, and an imaging device 92 for imaging the target may be provided in addition to the detection optical fiber bundle portion 65.

The detection optical fiber bundle portion 65 has the same configuration as that in the first embodiment, and the optical characteristic converting portion 101 is formed at a predetermined position of the insertion portion 3. A light amount converted in the optical characteristic converting portion 101 is received by the shape sensor light receiving portion 63.

Figure 14:
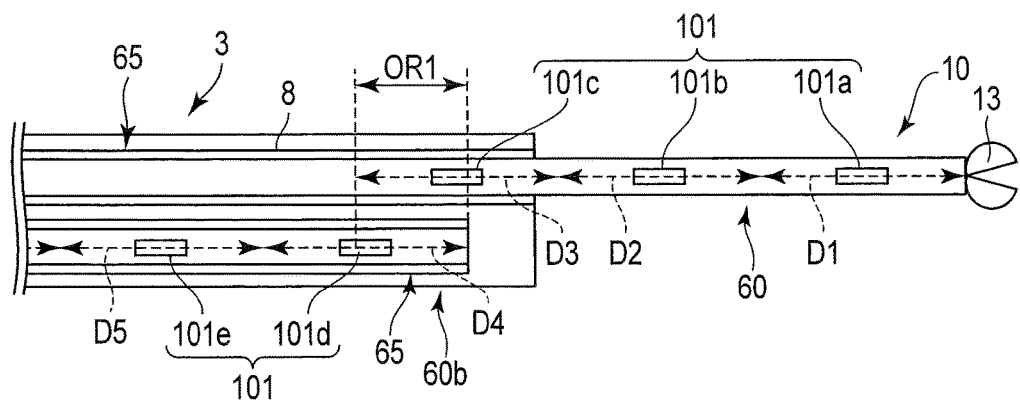
FIG. 14 is a schematic configuration diagram showing detection ranges of an insertion member and an optical characteristic converting portion of the flexible insertion portion according to the second embodiment.

The positional relation between the first shape sensor 60 for detecting the shape (curving state) of the insertion member 10 and the second shape sensor 60b for detecting the curving state of the insertion portion 3 is described with reference to FIG. 14. In FIG. 14, D1, D2, and D3 indicate detection ranges of three optical characteristic converting portions 101 (101a, 101b, and 101c) of the first shape sensor 60, and D4 and D5 indicate detection ranges of two optical characteristic converting portions 101 (101d and 101e) of the second shape sensor 60b. In the range in which the insertion member 10 can be inserted, the optical characteristic converting portions 101 which are curving detecting portions are provided so that the detection ranges of the first shape sensor 60 overlaps the detection ranges of the second shape sensor 60b.

The detection ranges D1, D2, D3, D4, and D5 of the optical characteristic converting portions 101 are disposed so that one of the detection ranges D1, D2, and D3 of at least the optical characteristic converting portions 101 of the first shape sensor 60 overlaps one of the detection ranges D4 and D5 of at least the optical characteristic converting portions 101 of the second shape sensor 60b. For example, as shown in FIG. 14, there is a range OR1 in which the detection range D3 of the optical characteristic converting portion 101c of the first shape sensor 60 overlaps the detection range D4 of the optical characteristic converting portion 101d of the second shape sensor 60b. Thus, the shapes of the insertion portion 3 and the insertion member 10 can be detected as a continuous shape by the first shape sensor 60 and the second shape sensor 60b.

Here, the detection ranges of the optical characteristic converting portions 101 of the first shape sensor 60 and the second shape sensor 60b are described. Each of the optical characteristic converting portions 101 detects the curving state by themselves. However, actually, the part of the optical characteristic converting portion 101 having a length of, for example, 3 mm in the longitudinal direction alone is not curved due to the configurations and materials of the insertion portion 3 and the insertion member 10 in which the first shape sensor 60 and the second shape sensor 60b are incorporated. The peripheral part of the optical characteristic converting portion 101, for example, a certain range in the longitudinal direction of the optical characteristic converting portion 101, for example, a peripheral member in a range of 60 mm curves together.

Therefore, the optical characteristic converting portion 101 substantially has certain ranges, for example, detection ranges of 30 mm from the center of the optical characteristic converting portion 101 to each of the distal and rear sides. If a wide detection range of the optical characteristic converting portion 101 is set, the accuracy of shape detection deteriorates. On the other hand, if the detection range is narrower, the accuracy improves, but the number of optical fibers necessary for desired detection increases, and the configurations of the first shape sensor 60 and the second shape sensor 60b are complicated. Thus, it is preferable to set a wide range that does not cause problems to the shape detection.

Figure 15:
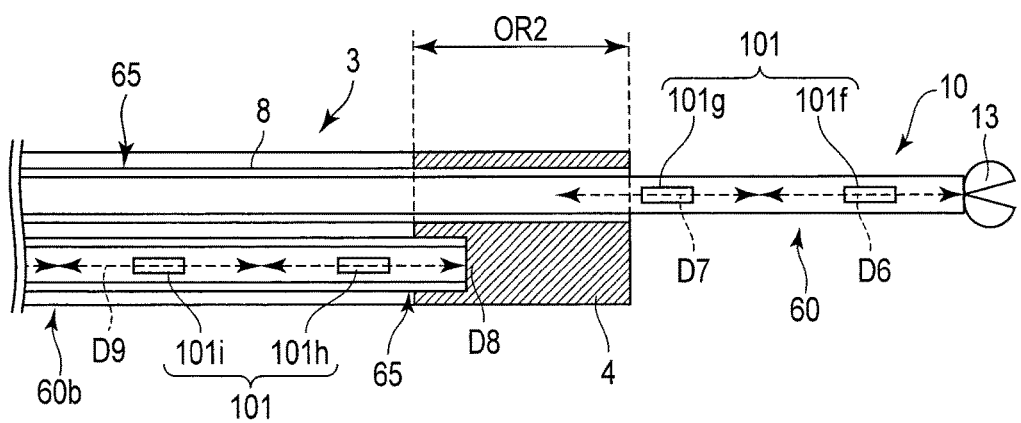
FIG. 15 is a schematic configuration diagram showing detection ranges of the insertion member and the optical characteristic converting portion of the flexible insertion portion according to the second embodiment when the distal end of the flexible insertion portion is a hard member.

When detection ranges D6, D7, D8, and D9 of the optical characteristic converting portions 101 include the hard distal portion 4 as shown in FIG. 15, the detection ranges D6, D7, D8, and D9 of the optical characteristic converting portions 101 do not need to be disposed to overlap in the actual detection ranges because the distal portion 4 does not curve. In this case, if the detection ranges of the optical characteristic converting portions 101 disposed at both ends of the distal portion 4 overlap the range of the hard member, the insertion portion 3 and the insertion member 10 can be calculated as a continuous shape. For example, if the detection range D7 of the optical characteristic converting portion 101g of the insertion member 10 and the detection range D8 of the optical characteristic converting portion 101h of the insertion portion 3 each include the range of the distal portion 4 as shown in FIG. 15, the detection ranges substantially behave as if overlapping in a range OR2 of the hard portion 4 because the range of the distal portion 4 does not curve.

In the present embodiment, the light source portion 61 further has a function of separately applying light to the first shape sensor 60 and the second shape sensor 60b. The shape sensor light receiving portion 63 further has a function of separately receiving the light amount guided from the side of the insertion member 10 and the light amount guided from the side of the insertion portion 3. The light transmission amount received by the shape sensor light receiving portion 63 is sent to the calculation unit 40. The shape sensor light source units 61 and the shape sensor light receiving portions 63 may be separately disposed for the first shape sensor 60 and the second shape sensor 60b.

The calculation unit 40 further has a function of calculating the position of the distal end of the insertion portion 3 and the shape of the insertion portion 3, and calculating operation support information for the desired insertion portion 3. The calculation unit 40 may also have a function of adding or subtracting specification data regarding each part of the flexible insertion portion 2, for example, the dimensions of the insertion portion 3 to or from the position of the distal end of the insertion member 10 and the shape of the insertion member 10, and more accurately calculating operation support information for the insertion portion 3 and the insertion member 10. Here, the operation support information for the desired insertion portion 3 is the operation support information for at least one of the detection start position of the state detector 160 and the rotation amount of the insertion portion 3 with respect to the insertion hole of the specimen 120.

As in the first embodiment described above, the calculation unit 40 according to the present embodiment multiplies coefficients $a_s$ and $b_s$ that take into consideration the coefficient of each direction to calculate an insertion amount $m_{s0}$ and a rotation amount $\theta_{s0}$. Here, the rotation amount $\theta_{s0}$ is calculated with respect to the above-mentioned second rotation reference position at which the third mark 73 and the fourth mark 74 are adjusted to each other.

An insertion amount correction value Ls of the flexible insertion portion 2 which is the distance between the location of the state detector 160 and the insertion hole of the specimen 120 is found in advance. Therefore, an insertion amount $m_{s1}$ of the distal end of the insertion portion 3 from the insertion hole of the specimen 120 is calculated from the difference between the correction value Ls and the insertion amount $m_{s0}$ of the insertion member 10.

An expression that shows the relation between change amount of the light amount and the curving amount of the insertion portion 3 detected by the second shape sensor 60b is found in advance. Therefore, the curving amount of the insertion member 10 is calculated from the light amount of the second shape sensor 60b.

From the calculation results, a calculation result of a desired direction can be selectively output. Equation 5 which is a computational expression of the insertion amount, Equation 6 which is a computational expression of the rotation amount, Equation 7 which is a computational expression of the insertion amount $m_{s1}$ from the insertion hole of the specimen 120, and Equation 8 which is a computational expression of a curving amount $\Phi_s$ of a curving portion of the insertion portion 3 are shown below. That is, the calculation unit 40 repeats the above-mentioned processing, and integrates the displacement amounts of the coordinates of given successive detection times, and thereby calculates an insertion amount and a rotation amount of the insertion portion 3 from a given detection time to the desired detection time.

$$m_{s0} = a_s \times \Delta z \quad (5)$$

wherein $m_{s0}$ is the insertion amount from the time $t_{n-1}$ to the time $t_n$, $\Delta z$ is a coordinate difference in the direction of the z-axis 83 regarding the pattern to which the image data from the time $t_{n-1}$ to the time $t_n$ corresponds, and $a_s$ is an insertion amount conversion coefficient.

$$\theta_{s0} = b_s \times \Delta x \quad (6)$$

wherein $\theta_{s0}$ is the rotation amount from the time $t_{n-1}$ to the time $t_n$, $\Delta x$ is a coordinate difference in the direction of the x-axis 81 regarding the pattern to which the image data from the time $t_{n-1}$ to the time $t_n$ corresponds, and $b_s$ is a rotation amount conversion coefficient.

The calculated insertion amount $m_{s0}$ is a movement amount from the time $t_0$ at which the state detector 160 has started detection to a given time $t_n$. The net insertion amount $m_{s1}$ of the insertion portion 3 is calculated by the difference between the calculated insertion amount $m_{s0}$ and the correction value Ls.

$$\theta_{s0} = b_s \times \Delta x \quad (7)$$

wherein $L_s$ is the correction value of the insertion amount of the insertion member, $m_{s0}$ is the insertion amount from the time $t_{n-1}$ to the time $t_n$, and $m_{s1}$ is the net insertion amount.

The calculation unit 40 can also calculate the curving amount $\Phi_s$ of the curving portion of the insertion portion 3. The curving amount $\phi_s$ of a curving detector is calculated by the use of a change $\Delta l_s$ in the light transmission amount of the shape sensor 60b.

$$\Phi_s = f(\Delta l_s) \quad (8)$$

wherein $\Phi_s$ is the curving amount of the curving portion of the insertion portion 3, and $\Delta l_s$ is the change in the light transmission amount.

In the present embodiment, the insertion portion 3 is inserted through the state detector 160 disposed in the vicinity of the specimen 120, and then inserted into the specimen 120.

When the insertion portion 3 is inserted into the state detector 160, the state detector 160 starts detection in the same manner as the detector 20 according to the first embodiment. The detected information regarding the detection start position and the detected information for calculating an insertion amount and a rotation amount are sent to the calculation unit 40.

When the distal end of the insertion portion 3 is curved, the light transmission amount received by the shape sensor light receiving portion 63 is changed by the optical characteristic converting portion 101 disposed at a predetermined detection position. This light transmission amount is sent to the calculation unit 40 in such a manner as to separate the insertion member 10 and the insertion portion 3 from each other.

The calculation unit 40 calculates operation support information for the insertion member 10 and the insertion portion 3 on the basis of the information from the state detector 20, the storage unit 30, the shape sensor 60, and the second shape sensor 60b. The display unit 50 displays the operation support information calculated by the calculation unit 40. According to the present embodiment, the insertion system 1 is provided with the state detector 160, so that the insertion amount and rotation amount of the insertion portion 3 relative to the specimen 120 can be calculated.

The state detector 160 has the third mark 73, so that it is possible to visually recognize the insertion position with ease for alignment in the rotation direction by adjusting the third mark 73 to the fourth mark 74 formed on the outer circumference of the insertion portion 3.

The flexible insertion portion 2 has the shape sensor 60b, and detects the shape of the flexible insertion portion 2. The optical characteristic converting portion 101 of the first shape sensor 60 and the optical characteristic converting portion 101 of the second shape sensor 60b are disposed so that the detection ranges of the optical characteristic converting portions 101 for the flexible insertion portion 2 and the insertion member 10 overlap. Thus, the shapes of the flexible insertion portion 2 and the insertion member 10 can be calculated as a continuous shape. That is, the shape of the insertion member 10 and the position of the distal end from the insertion hole of the specimen 120 can be detected.

The calculation unit 40 is configured to calculate the positions of the distal ends of the insertion member 10 and the insertion portion 3 from the insertion hole of the specimen 120 and the shape in the specimen 120 in the present embodiment. However, the calculation unit 40 has a function of calculating the amount of insertion of the insertion portion 3 into the specimen 120 from the amount of insertion of the insertion member 10 into the specimen 120 and from the amount of insertion of the insertion portion 3 into the specimen 120.

For the rotation amount relative to the rotation reference position as well, the calculation unit 40 may calculate the rotation amount of the insertion member 10 relative to the second rotation reference position from the rotation amount of the insertion member 10 relative to the first rotation reference position and from the rotation amount of the insertion portion 3 relative to the second rotation reference position.

Furthermore, the insertion portion 3 of the flexible insertion portion 2 is a flexible device by way of example in the present embodiment. However, the insertion portion 3 may be hard as in a first modification shown in FIG. 16. In this case, it is not necessary to provide the second shape sensor 60b, and the shape of the insertion member 10 relative to the specimen 120 is calculated from the insertion amount and rotation amount of the hard insertion portion 3 relative to the specimen 120 and from the shape of the insertion member 10 relative to the hard insertion portion 3. Thus, if the insertion portion 3 is hard, it is not necessary to detect the shape of the insertion portion 3, and the calculation of the shape of the insertion member 10 relative to the specimen 120 is easier.

If the detection range of the first shape sensor 60 allows detection from the insertion hole of the specimen 120 to the distal end of the insertion portion 3, the flexible insertion portion 2 does not need to be provided with the second shape sensor 60b either. The shape of the insertion portion 3 relative to the specimen 120 and the shape of the insertion member 10 relative to the specimen 120 may be calculated from the insertion amount and rotation amount of the insertion portion 3 relative to the specimen 120, the insertion amount and rotation amount of the insertion member 10 relative to the insertion portion 3, and the shape of the insertion member 10.

The entrance portion of the insertion channel to insert the insertion member 10 is curved in the first modification shown in FIG. 16, but may be shaped straight.

Moreover, if the insertion member 10 and the insertion portion 3 do not need to be detected as a continuous shape in the present embodiment, the optical characteristic converting portions 101 for the insertion member 10 and the insertion portion 3 do not need to be disposed so that the detection ranges overlap.

A second modification of the second embodiment is described with reference to FIG. 17.

The insertion system 1 according to the present modification has a configuration substantially equivalent to that of the insertion system 1 according to the second embodiment, but is different in configuration in that it has a state detector (second state detector) 170 which magnetically detects the curving state of the insertion portion 3. Therefore, components equivalent to those in the insertion system 1 according to the second embodiment are provided with the same reference signs, and are not described in detail.

Figure 17:
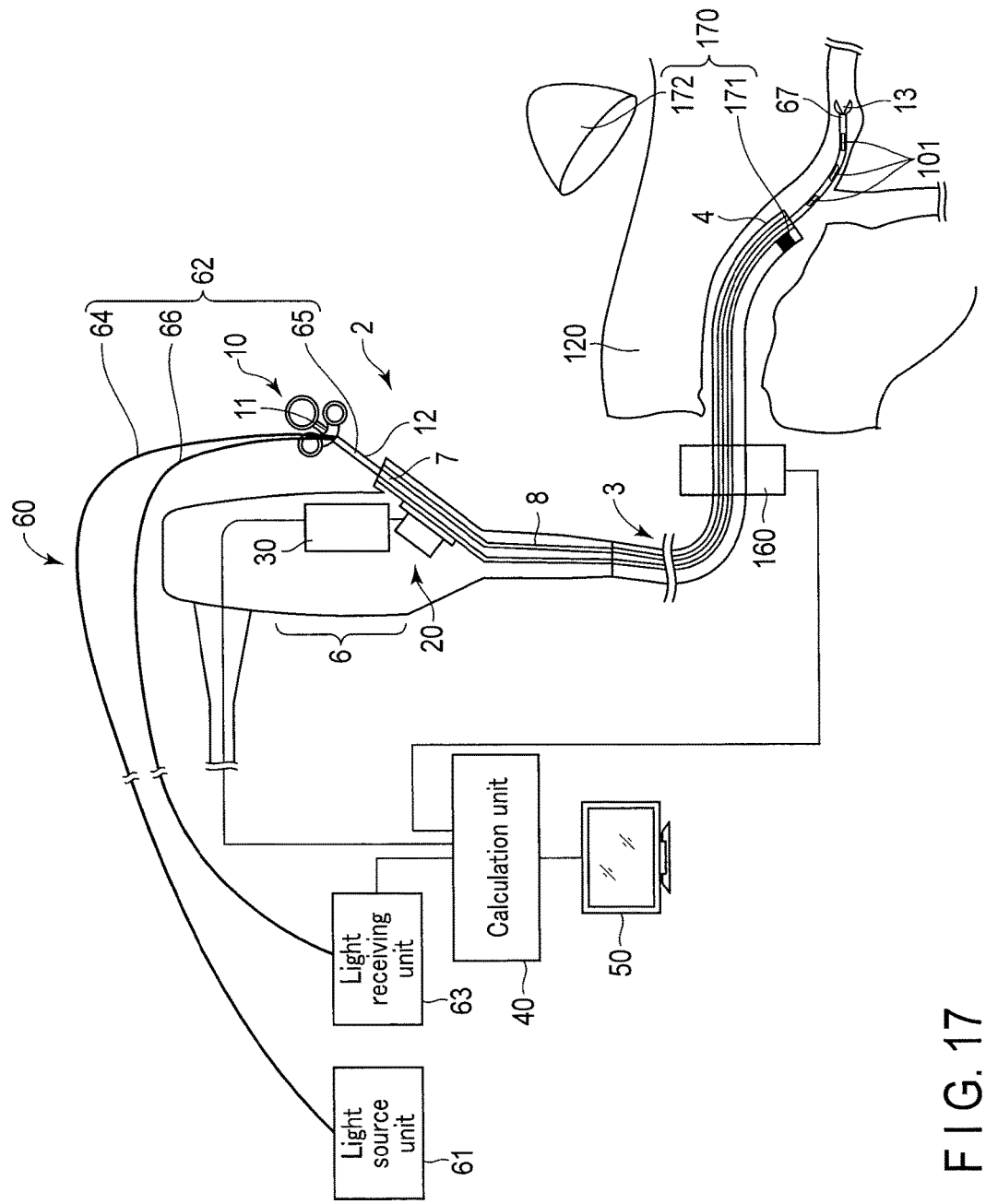
FIG. 17 is a schematic configuration diagram of an insertion system according to a second modification of the second embodiment.

As shown in FIG. 17, the state detector 170 according to the present modification has a transmitter 171 which generates a magnetic field, and a receiver 172. The transmitter 171 is disposed inside the insertion portion 3 in the vicinity of its distal end. The receiver 172 is disposed outside the specimen 120.

The transmitter 171 is, for example, a coiled member, and is configured to generate a magnetic field when an electric current is passed.

The receiver 172 has a function of detecting the strength and direction of the magnetic field of the transmitter 171, and detecting the position and direction of the distal end of the insertion portion 3 relative to the receiver 172. Here, the direction of the distal end is a direction in which the insertion member 10 exits from the distal end of the insertion portion 3. The receiver 172 is, for example, an antenna. Information regarding the position and direction of the distal end of the insertion portion 3 detected by the receiver 172 is sent to the calculation unit 40.

On the other hand, the position and pose of the specimen 120 relative the receiver 172 may be input by, for example, unshown input means. Alternatively, a coil for detecting the position of the specimen 120 may be disposed in the specimen 120, and the position and pose of the specimen 120 relative the receiver 172 may be detected. Information regarding the position and pose of the specimen 120 relative the receiver 172 is input or sent to the calculation unit 40.

The calculation unit 40 has a function of calculating operation support information which includes the position and direction of the distal end of the insertion portion 3 relative to the specimen 120 from the position and direction of the distal end of the insertion portion 3 relative to the receiver 172 sent from the receiver 172 and from the position and pose of the specimen 120 relative the receiver 172. The calculation unit 40 further has a function of calculating operation support information which includes the insertion amount and rotation amount of the insertion member 10 from the position of the distal end of the insertion portion 3 relative to the specimen 120 from the calculated position and direction of the distal end of the insertion portion 3 relative to the specimen 120 and from the insertion amount and rotation amount of the insertion member 10. The calculation unit 40 further has a function of calculating operation support information which includes the shape of the insertion member 10 relative to the specimen 120 from the position of the distal end of the insertion portion 3 relative to the specimen 120, from the insertion amount and rotation amount of the insertion member 10, and from the shape of the insertion member 10.

As described above, according to the second modification, the position and direction of the distal end of the insertion portion 3 can be directly detected by the state detector 170. Thus, detection errors are reduced. Even if the insertion portion 3 is longer, detection errors do not easily occur. The state detector 170 is a detector which detects magnetically in the second modification, but may be an acceleration sensor.

A third modification of the second embodiment is described with reference to FIG. 18.

The insertion system 1 according to the third modification has a configuration substantially equivalent to that according to the second embodiment or the first modification of the second embodiment, but is different in configuration in that it has a rotation reference position detector (second rotation reference position detector) 180 which detects the rotation reference position of the insertion portion 3.

Figure 18:
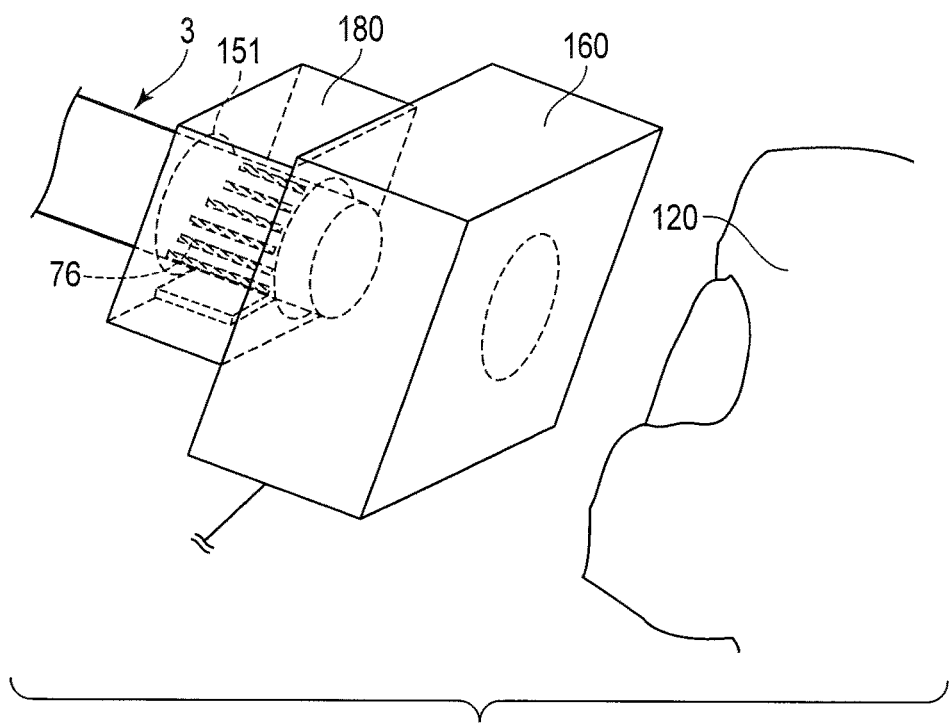
FIG. 18 is a perspective view of a rotation reference position detector of a flexible insertion portion in an insertion system according to a third modification of the second embodiment.

As shown in FIG. 18, an optical index (second rotation index) 76 which indicates a rotation position is provided on the outer circumferential surface of the insertion portion 3. The rotation reference position detector 180 according to the present modification has a configuration substantially equivalent to that of the rotation reference position detector 150 according to the second modification of the first embodiment, but is different in, for example, size and location.

The rotation reference position detector 180 according to the present modification is detachably disposed in close contact with the insertion hole 7 of the state detector 160 according to the second embodiment described above. The rotation reference position detector 180 has the bore (opening) 151 through which the insertion portion 3 is inserted. The rotation reference position detector 180 has a function of detecting the optical index 76 of the insertion portion 3 inserted in the bore 151 of the rotation reference position detector 180, and defining the detected shape, for example, the position of the length of a line as the rotation reference position.

The calculation unit 40 can calculate the absolute value of the rotation amount of the insertion portion 3 from the rotation reference position defined by the rotation reference position detector 180 and from the detection result (a displacement amount or a rotation amount) by the state detector 160.

According to the present modification, the rotation amount of the insertion portion 3 from the rotation reference position can be calculated, so that it is not necessary to adjust the rotation reference position at the beginning, and the insertion portion 3 can be easily inserted. The rotation reference position is mechanically defined, and the rotation amount of the insertion portion 3 is calculated, so that more accurate operation support information can be acquired. In the present modification, the state detector 160 may have the function of the rotation reference position detector 180. That is, the state detector 160 may detect the optical index 76.

Furthermore, some of the following can be acquired as the operation support information calculated by the calculation unit 40: the correction value of the insertion amount of the insertion member 10, the insertion amount and rotation amount of the insertion member 10 detected by the state detector 160, the reference position of the rotation direction of the insertion member 10 detected by the rotation reference position detector 150, the shape of the insertion member 10 detected by the first shape sensor 60, the correction value of the insertion amount of the insertion portion 3, the insertion amount and rotation amount of the insertion portion 3 detected by the state detector 170, the rotation reference position of the insertion portion 3 in the rotation direction detected by the state detector 170, the shape of the insertion portion 3 detected by the second shape sensor 60b, and the position and direction of the distal end of the insertion portion 3 detected by the state detector 170. Operation support information can also be calculated by the combination of the above.

The insertion system according to each of the embodiments of the present invention has advantageous effects of being able to accurately recognize the insertion position and insertion direction of the insertion member by detecting operation support information such as an insertion amount and a rotation amount of the insertion member, and the position and shape of the distal end.

[Additional Notes]

The embodiments of the present invention described above include the contents described in the following additional notes.

[1] An insertion portion including at least a grasp portion, an insertion portion to be inserted into a specimen, an insertion channel passing from the proximal end of the insertion portion to the distal end thereof, and a first state detector which is disposed in the insertion portion and which detects at least one of an insertion amount of the inserted insertion member in an insertion direction along a longitudinal direction and a rotation amount of the insertion member around its axis along the insertion direction.

[2] The insertion portion according to (1), including a second shape sensor which has at least one optical characteristic converting portion disposed at a predetermined position and which is equipped with at least one optical fiber sensor and which detects a bending state.

[3] The insertion portion according to (1), including optical fiber sensors, two of the optical fiber sensors being applied as a pair of sensors to detect bending in two directions.

[4] The flexible insertion portion according to (1), (2), and (3) which is an endoscope.

According to the above configuration in [1] to [4], it is also possible to use a single flexible insertion portion, for example, a single endoscope as an endoscope that calculates no operation support information as heretofore. It is also possible to improve operability by combining calculation units to calculate at least one of an insertion amount of the insertion member to be inserted into the insertion channel and a rotation amount of the insertion member around its axis along the insertion direction. It is also possible to apply a combination of an insertion member having a shape sensor and a state detector which detects an insertion amount of the insertion portion or a rotation amount of the insertion member around its axis along the insertion direction, and thereby calculate operation support information such as the amount of insertion of the insertion portion into a specimen, the rotation amount of the insertion member around its axis along the insertion direction, and/or the curving shape of the insertion member relative to the specimen.

[5] An insertion member including a first shape sensor which is equipped with at least one optical fiber sensor provided with at least one optical characteristic converting portion disposed at a predetermined position and which detects a bending state.

[6] The insertion member according to (1), including optical fiber sensors, two of the optical fiber sensors being applied as a pair of sensors to detect bending in two directions that intersect at right angles.

[7] The insertion member according to any one of (5) and (6) which is a treatment instrument.

According to the above configuration in [5] to [7], it is also possible to use a single insertion member, for example, a treatment instrument as a treatment instrument that calculates no operation support information as heretofore. It is also possible to improve operability by combining calculation units to calculate curving shape of the treatment instrument. It is also possible to apply a combination of the first state detector, the insertion portion having the second shape sensor, and a state detector which detects an insertion amount of the insertion portion and a rotation amount of the insertion member around its central axis along the insertion direction of the insertion member, and thereby calculate operation support information such as the amount of insertion of the insertion member into the specimen, the rotation amount, and/or the curving shape of the insertion member relative to the specimen.

[8] An insertion system characterized by including the flexible insertion portion, the insertion member to be inserted into the insertion channel of the flexible insertion portion, the first state detector which detects inserted insertion member, a second state detector which is disposed in the specimen and which detects at least one of an insertion amount of the flexible insertion portion and a rotation amount of the insertion member around its central axis along the insertion direction of the insertion portion, the first shape sensor, and a calculation unit which calculates operation support information from at least one detection result by the second shape sensor.

[9] The insertion system according to (8) which is an endoscope system.

According to the above configuration in [8] to [9], it is possible to calculate operation support information and improve operability as shown in the embodiments.

According to the above configuration in [8] to [9], it is possible to calculate operation support information and improve operability as shown in the embodiments.

What is claimed is:

1. An insertion system comprising:
   an insertion portion including at least a grasp portion and an insertion channel passing inside the insertion portion from a proximal end of the insertion portion to a distal end of the insertion portion, the insertion portion being configured to be inserted into a specimen;
   an insertion member configured to be inserted into an insertion hole of the insertion channel on a side of the proximal end of the insertion portion, and projected from a side of the distal end of the insertion portion to extend into the specimen;
   an optical pattern provided on an outer circumferential surface of the insertion member;
   a first sensor disposed in the insertion hole of the insertion portion, the first sensor being configured to read the optical pattern of the insertion member inserted in the insertion channel and to detect an insertion amount of the inserted insertion member and a rotation amount of the insertion member around its central axis in the insertion portion; and
   a processor comprising hardware, the processor being configured to calculate, from a detection result by the first sensor, the insertion amount, the rotation amount, and a position and a shape of a distal end of the insertion member inserted through the insertion channel.

2. The insertion system according to claim 1, wherein the first sensor is disposed in parallel with the insertion channel in the grasp portion.

3. The insertion system according to claim 1, wherein the processor is configured to calculate a net insertion amount of the insertion member which is a length from the distal end of the insertion portion to the distal end of the insertion member, from an insertion amount correction value which is a length from a detection position of the first state detector to the distal end of the insertion portion, and from the insertion amount of the insertion member.

4. The insertion system according to claim 1, wherein a hole through which the first sensor passes and an opening of the insertion hole of the insertion channel are disposed such that centers of the hole and the opening are coaxial, and the insertion member is inserted through the hole and the insertion channel.

5. The insertion system according to claim 1, wherein the optical pattern comprises:
   a first mark formed in an end face of an insertion hole of the insertion channel for indicating a rotation reference position of the insertion member; and
   a second mark formed in the insertion member along the longitudinal direction of the outer circumferential surface of the insertion member so that the direction and position of the second mark are adjusted to the direction and position of the first mark to allow the insertion member to be disposed at a predetermined rotation reference position when the insertion member is inserted into the insertion channel.

6. The insertion system according to claim 1, wherein the insertion member comprises a shape sensor which is flexible and disposed in the insertion member, the shape sensor being configured to detect a curving state of the insertion member.

7. The insertion system according to claim 6, wherein the shape sensor comprises:
   a light source,
   a light guide member which guides light emitted from the light source into parts and which has an optical characteristic converting portion to convert the characteristics of at least one light, and
   a light receiving portion which detects the changes of the characteristics of the light in the light guide member.

8. The insertion system according to claim 6, wherein the first sensor is configured to detect information to calculate at least one of an insertion amount from a start position to the distal end of the insertion member, and a rotation amount of the insertion member around its central axis along the insertion direction, and the processor is further configured to calculate at least one of the position of the distal end of the insertion member and the shape of the insertion member from at least one of an insertion amount which is a length from the distal end of the insertion portion to the distal end of the insertion member and a rotation amount relative to the insertion portion, and from the curving state detected by the first shape sensor.

9. The insertion system according to claim 1, further comprising a second sensor configured to detect information to calculate the rotation amount of the insertion portion relative to the specimen,
   the second sensor is configured to detect information which permits the rotation amount of the insertion member relative to the insertion portion to be calculated, and
   the processor is configured to calculate the rotation amount of the insertion member relative to the specimen from the rotation amount of the insertion portion relative to a rotation reference position of the specimen and from the rotation amount of the insertion member relative to the rotation reference position of the insertion portion.

10. The insertion system according to claim 1, further comprising:
    a distal position sensor disposed at the distal end of the insertion portion for detecting the position and direction of at least the distal end of the insertion portion relative to the specimen.

11. The insertion system according to claim 1, wherein the insertion portion is an endoscope.

* * * * *